United States Patent [19]

Mellin

[11] Patent Number: 5,854,282

[45] Date of Patent: Dec. 29, 1998

[54] 3-BENZOYL BENZOFURAN DERIVATIVES AS THYROID HORMONE ANTAGONISTS

[75] Inventor: Charlotta Mellin, Tullinge, Sweden

[73] Assignee: Karo Bio AB, Huddinge, Sweden

[21] Appl. No.: 776,924

[22] PCT Filed: Aug. 11, 1995

[86] PCT No.: PCT/EP95/03214

§ 371 Date: Apr. 7, 1997

§ 102(e) Date: Apr. 7, 1997

[87] PCT Pub. No.: WO96/05190

PCT Pub. Date: Feb. 22, 1996

[30] Foreign Application Priority Data

Aug. 11, 1994 [GB] United Kingdom .................. 9416219

[51] Int. Cl.⁶ .................................................. A61K 31/34
[52] U.S. Cl. ......................... 514/469; 549/468; 549/469
[58] Field of Search .................... 549/469, 468; 514/469

[56] References Cited

U.S. PATENT DOCUMENTS

| | | | |
|---|---|---|---|
| 4,255,585 | 3/1981 | Thuillier nee Nachmias et al. . | 549/58 |
| 4,851,554 | 7/1989 | Kennedy et al. ........................ | 549/471 |

FOREIGN PATENT DOCUMENTS 3261778  11/1991  Japan .

Primary Examiner—Amelia Owens
Attorney, Agent, or Firm—Todd E. Garabedian; Wiggin & Dana

[57] ABSTRACT

The invention provides compounds according to the formula

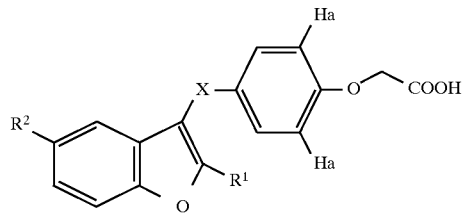

in which:

Ha=I or Br
X=$CH_2$ or C=O
$R^1$=$C_{1-4}$ alkyl
$R^2$=—$NHSO_2R^3$;
—$NHCOR^3$; or
—$NHCONHR^3$
where $R^3$=—$CF_3$, $C_{1-3}$ alkyl, 4-$R^4C_6H_4$—;
where $R^4$=$C_{1-4}$ alkoxy-; hydroxy-; fluoro-; or nitro-;
or a pharmaceutically acceptable salt thereof.

The compounds may particularly be used in the treatment of T3 regulated gene disorders and diseases.

9 Claims, 40 Drawing Sheets

3-BENZOYL BENZOFURAN DERIVATIVES AS THYROID HORMONE ANTAGONISTS

BACKGROUND OF THE INVENTION

1. Field of the Invention

This invention relates to organic compounds which function as nuclear receptor ligands and particularly as thyroid hormone antagonists.

2. Description of the Prior Art

Thyroid hormones have various effects on metabolism and oxygen consumption and in particular affect the heart. Thyroid hormones bind to nuclear thyroid hormone receptors. The complex formed by the thyroid hormone and the nuclear receptor binds to particular DNA patterns, termed "thyroid responsive elements" (TRE) in the promoter region of 3,5,3'-triiodothyronine (T-3)-regulated genes. The genes may be positively or negatively regulated.

In our International patent application no. PCT/SE92/00307, published as WO92/20331, we disclose a selection of organic compounds which can function as receptor ligands for T3 that is to say as thyroid hormone antagonists.

SUMMARY OF THE INVENTION

It is an object of the present invention to provide new and improved compounds and in particular compounds which can act as thyroid hormone antagonists.

According to one aspect of the present application there are provided compounds with the following general formula:

in which:
Ha=I or Br
X=$CH_2$ or C=O
$R^1$=$C_{1-4}$ alkyl
$R^2$=—$NHSO_2R^3$; $NHCOR^3$; or —$NHCONHR^3$
where $R^3$=—$CF_3$, $C_{1-3}$ alkyl, 4-$R^4C_6H_4$—;
where $R^4$=$C_{1-4}$ alkoxy-; hydroxy-; fluoro-; or nitro-;
or a pharmaceutically acceptable salt thereof.

For example, the compound may be selected from 2-n-Butyl-3-(3,5-diiodo-4-carboxymethoxybenzoyl)-5-trifluoromethylsulphonamidobenzofuran; 2-n-butyl-3,5-diiodo-4-carboxymethoxybenzoyl)-5-isopropylamidobenzofuran; 2-n-Butyl-3-(3,5-diiodo-4-carboxymethoxybenzoyl)-5-(4-methoxybenzamido) benzofuran; 2-n-Butyl-3-(3,5-diiodo-4-carboxymethoxybenzoyl)-5-(4-hydroxybenzamido) benzofuran; 2-Isopropyl-3-(3,5-diiodo-4-carboxymethoxybenzyl)-5-trifluoromethylsulphonamidobenzofuran; 2-isopropyl-3-(3,5-diiodo-4-carboxymethoxybenzoyl)-5-trifluoromethylsulphonamidobenzofuran; 2-Isopropyl-3-(3,5-diiodo-4-carboxymethoxybenzoyl)-5-(4-methoxybenzamido)benzofuran; 2-Isopropyl-3-(3,5-diiodo-4-carboxymethoxybenzoyl)-5-(4-hydroxybenzamido) benzofuran; 2-n-Butyl-3-(3,5-diiodo-4-carboxymethoxybenzoyl)-5-(4-fluorobenzamido) benzofuran; 2-Isopropyl-3-(3,5-diiodo-4-carboxymethoxybenzoyl)-5-(4-nitrobenzamido)benzofuran; 2-n-Butyl-3-(3,5-diiodo-4-carboxymethoxybenzoyl)-5-(4-methoxyphenylureido)benzofuran; 2-n-Butyl-3-(3,5-diiodo-4-carboxymethoxybenzoyl)-5-(4-hydroxyphenylureido) benzofuran; 2-n-Butyl-3-(3,5-dibromo-4-carboxymethoxybenzoyl)-5-(4-hydroxybenzamido) benzofuran; 2-Isopropyl-3-(3,5-dibromo-4-carboxymethoxybenzoyl)- 5-(4-methoxybenzamido) benzofuran; 2-Isopropyl-3-(3,5-dibromo-4-carboxymethoxybenzoyl)-5-(4-hydroxybenzamido) benzofuran.

The compound is preferably 2-n-Butyl-3-(3,5-diiodo-4-carboxymethoxybenzoyl)-5-(4-methoxybenzamido) benzofuran; or 2-n-Butyl-3-(3,5-diiodo-4-carboxymethoxybenzoyl)-5-(4-hydroxybenzamido) benzofuran.

The compounds of the present invention have an equal or better receptor binding affinity than the thyroid hormone antagonist compounds known in the prior art. The compounds of the present invention have not been described in the literature.

The compounds of the present invention may be used in the treatment of disorders which are dependent on the expression of T-3-regulated genes for example, heart arrhythymia, heart failure and hyperthyroidism.

According to another aspect of the present invention there is provided a pharmaceutical composition comprising an effective amount of a compound according to the present invention or a pharmaceutically effective salt thereof together with, if necessary, a suitable carrier.

According to another aspect of the present invention there is provided a method of treating a patient with a T-3-regulated gene disorder, comprising administering a compound according to the present invention or a pharmaceutically acceptable salt thereof, if necessary, in a suitable carrier, to the patient. The disorder may be for example, heart arrhythmia, heart failure, or hyperthyroidism.

DESCRIPTION OF THE FIGURES

The preparations of compounds in accordance with the present invention and tests on their activity will now be described, by way of example only, with reference to the following examples and the accompanying drawings, FIGS. 1–47 in which.

DETAILED DESCRIPTION OF THE INVENTION

PREPARATION OF COMPOUNDS

Figure 1:
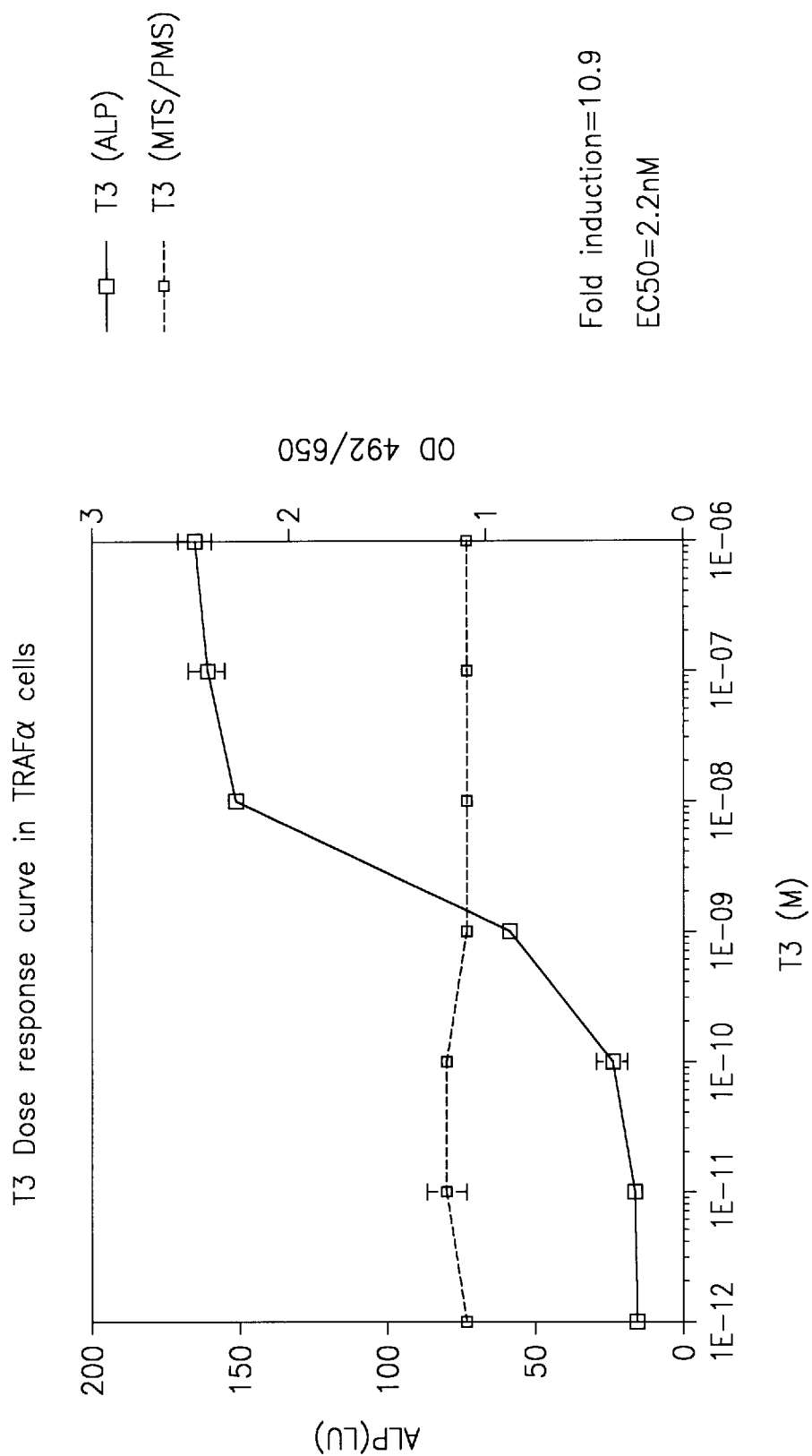
FIG. 1 is a T3 dose response curve in TRAP α cells.
Figure 2:
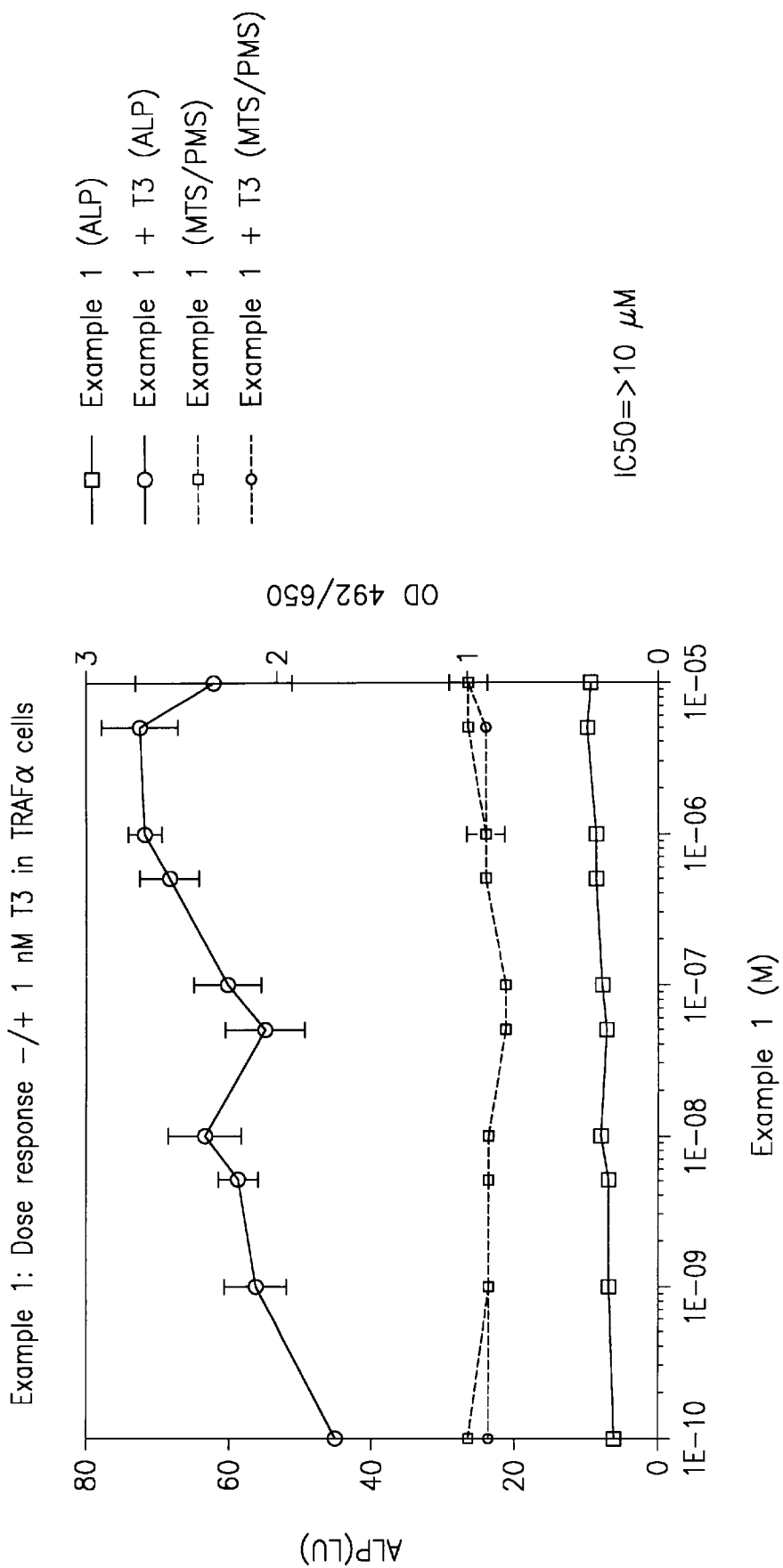
FIG. 2 illustrates the effects of 2-n-Butyl-3(3,5-diiodo-4-carboxymethoxybenzoyl)-5-trifluoromethylsulphonamidobenzofuran on TRAF α cells.
Figure 3:
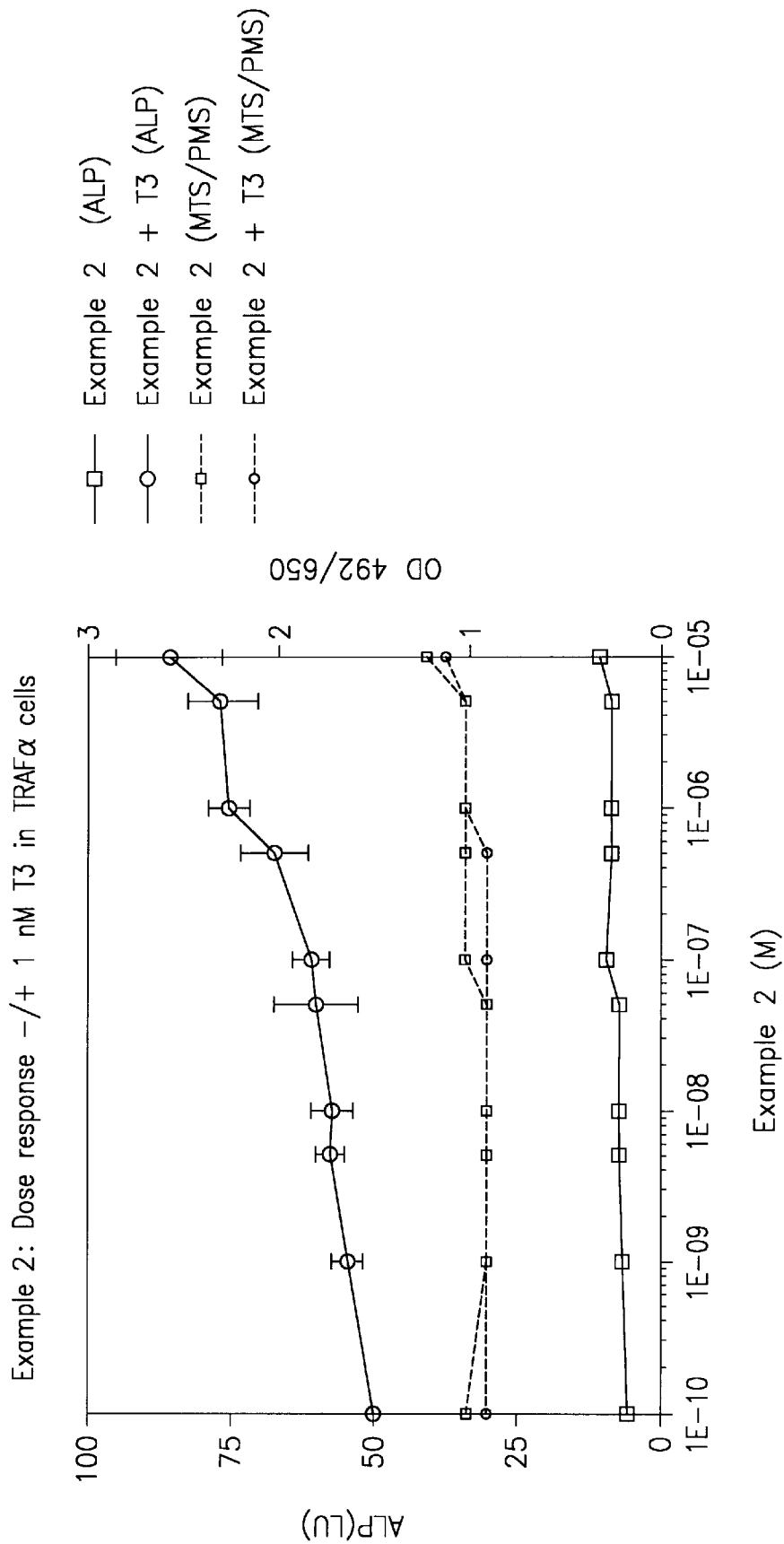
FIG. 3 illustrates the effects of 2-n-butyl-3,5-diiodo-4-carboxymethoxybenzoyl)-5-isopropylamidobenzofuran on TRAF α cells.
Figure 4:
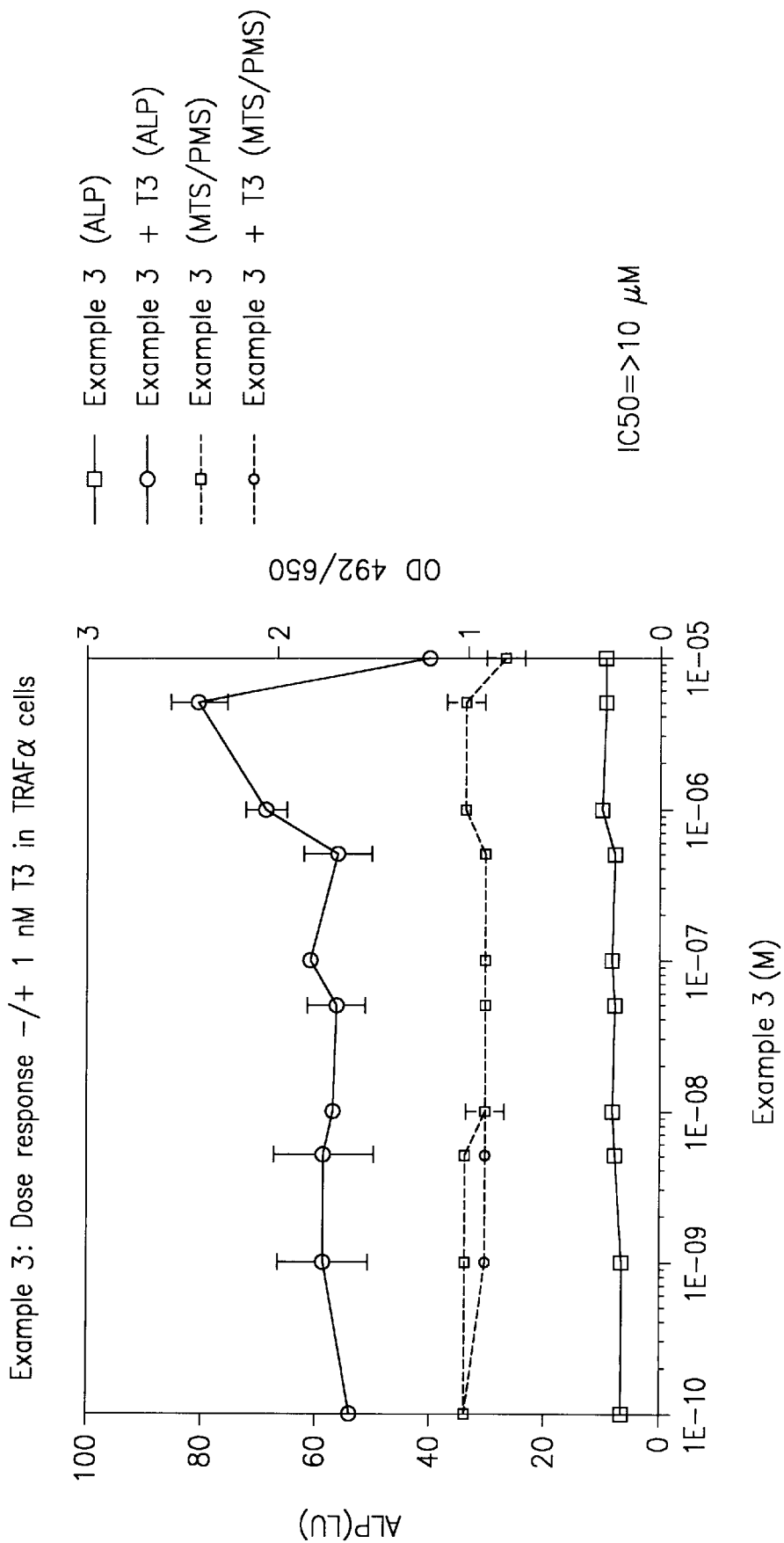
FIG. 4 illustrates the effects of 2-n-Butyl-3-(3,5-diiodo-4-carboxymethoxybenzoyl)-5-(4-methoxybenzamido) benzofuran on TRAF α cells.
Figure 5:
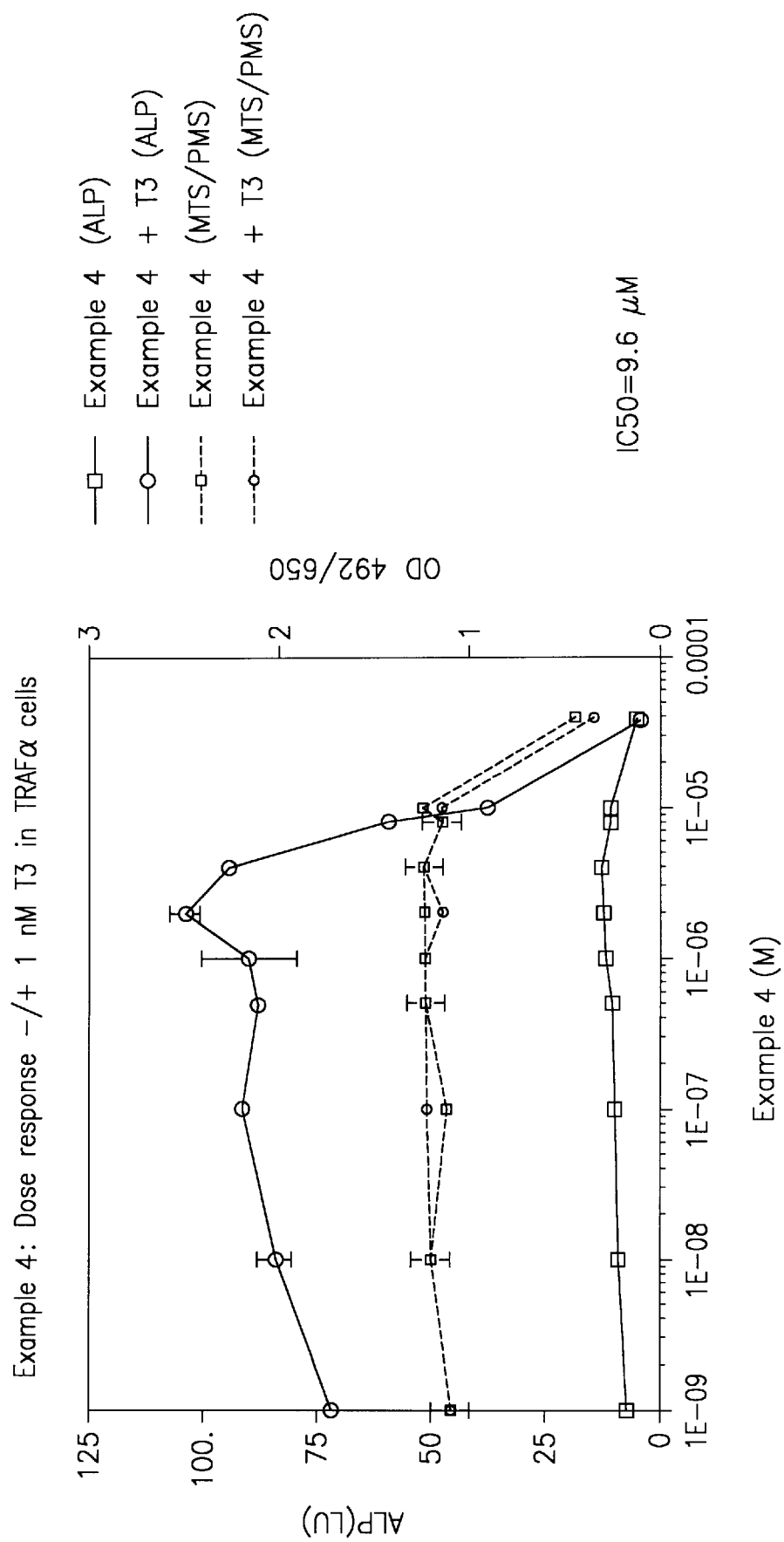
FIG. 5 illustrates the effects of 2-n-Butyl-3-(3,5-diiodo-4-carboxymethoxybenzoyl)-5-(4-hydroxybenzamido) benzofuran on TRAF α cells.
Figure 6:
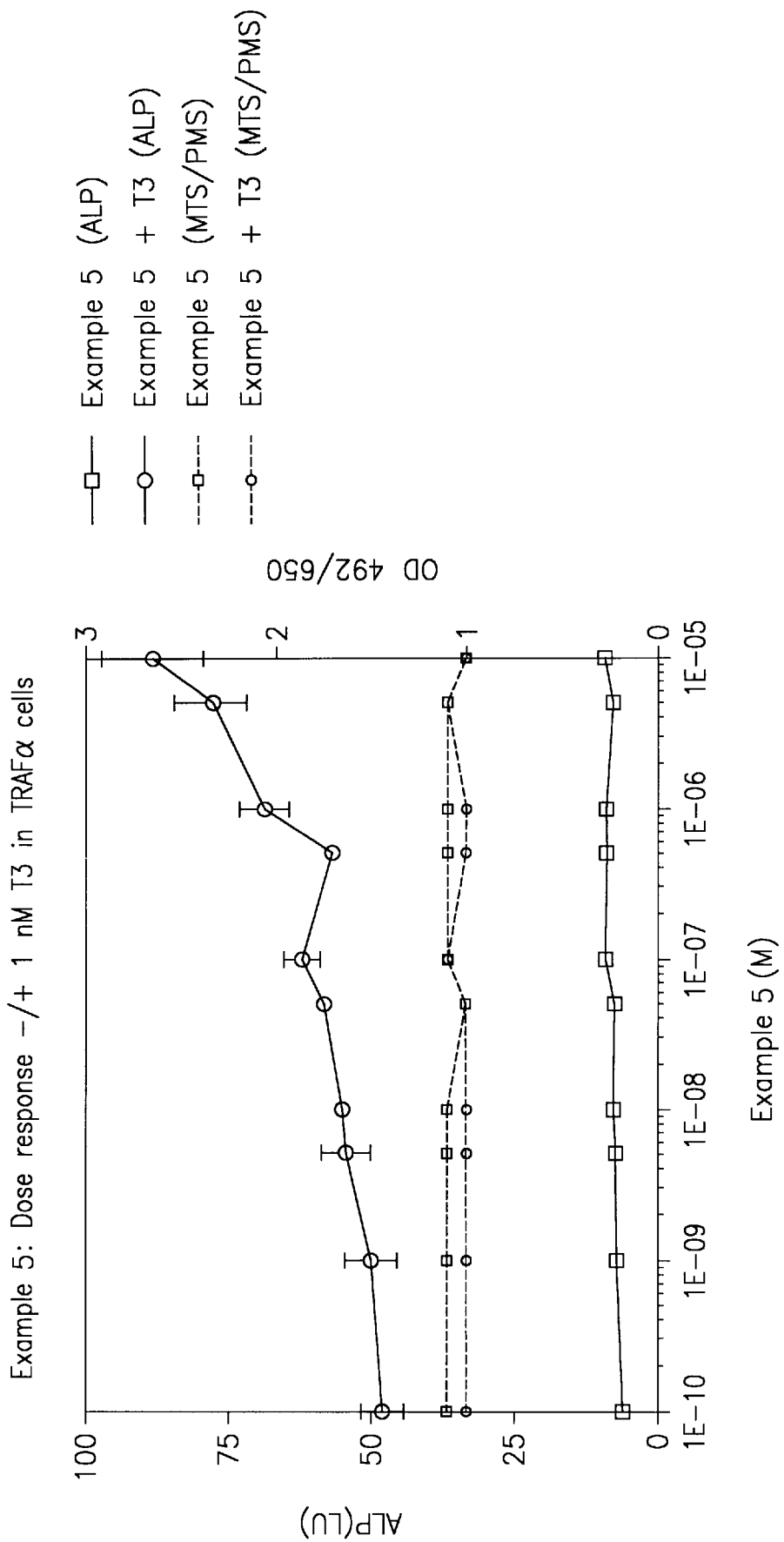
FIG. 6 illustrates the effects of 2-Isopropyl-3-(3,5-diiodo-4-carboxymethoxybenzyl)-5-trifluoromethylsulphonamidobenzofuran on TRAF α cells.
Figure 7:
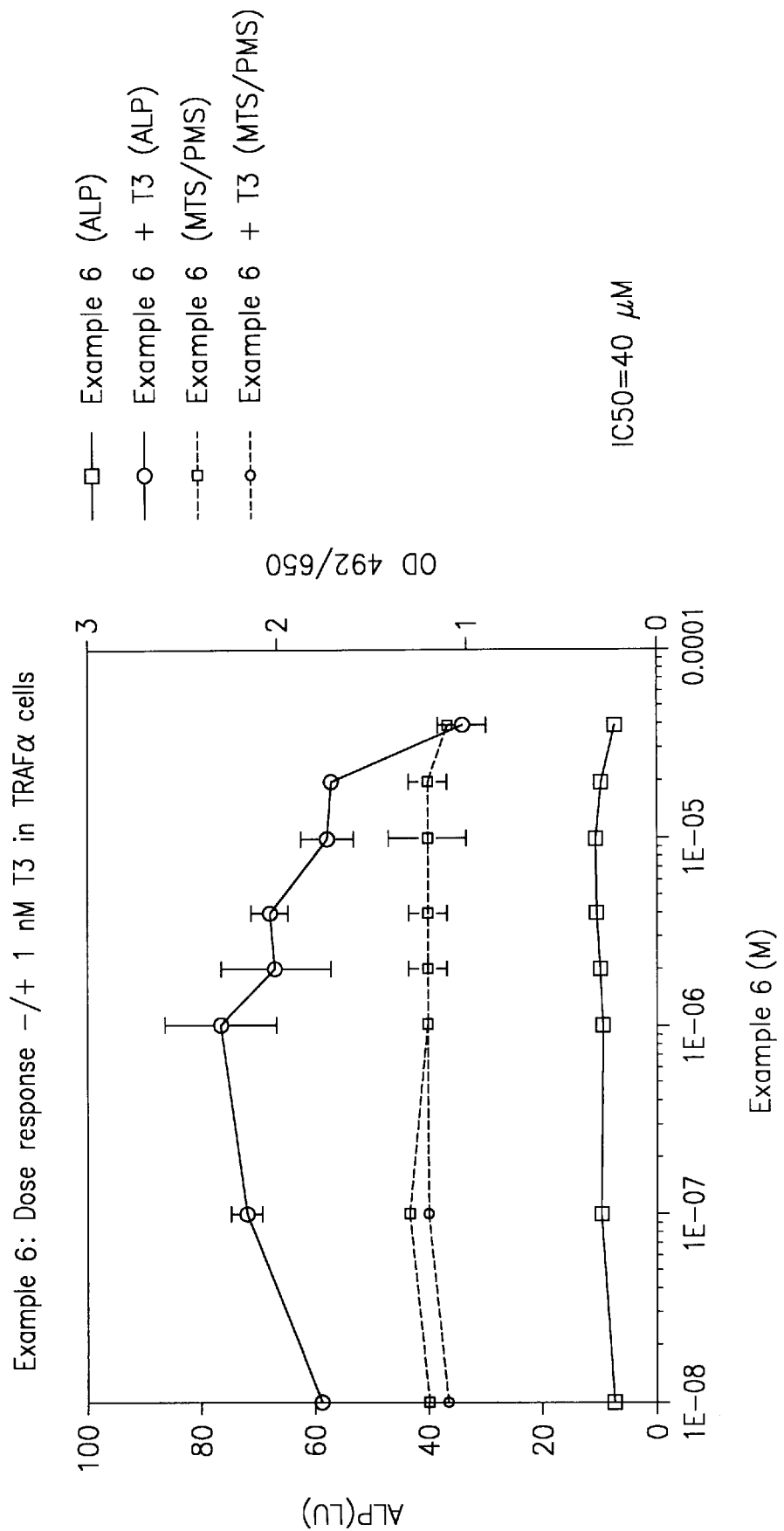
FIG. 7 illustrates the effects of 2-isopropyl-3-(3,5-diiodo-4-carboxymethoxybenzoyl)-5-trifluoromethylsulphonamidobenzofuran on TRAF α cells.
Figure 8:
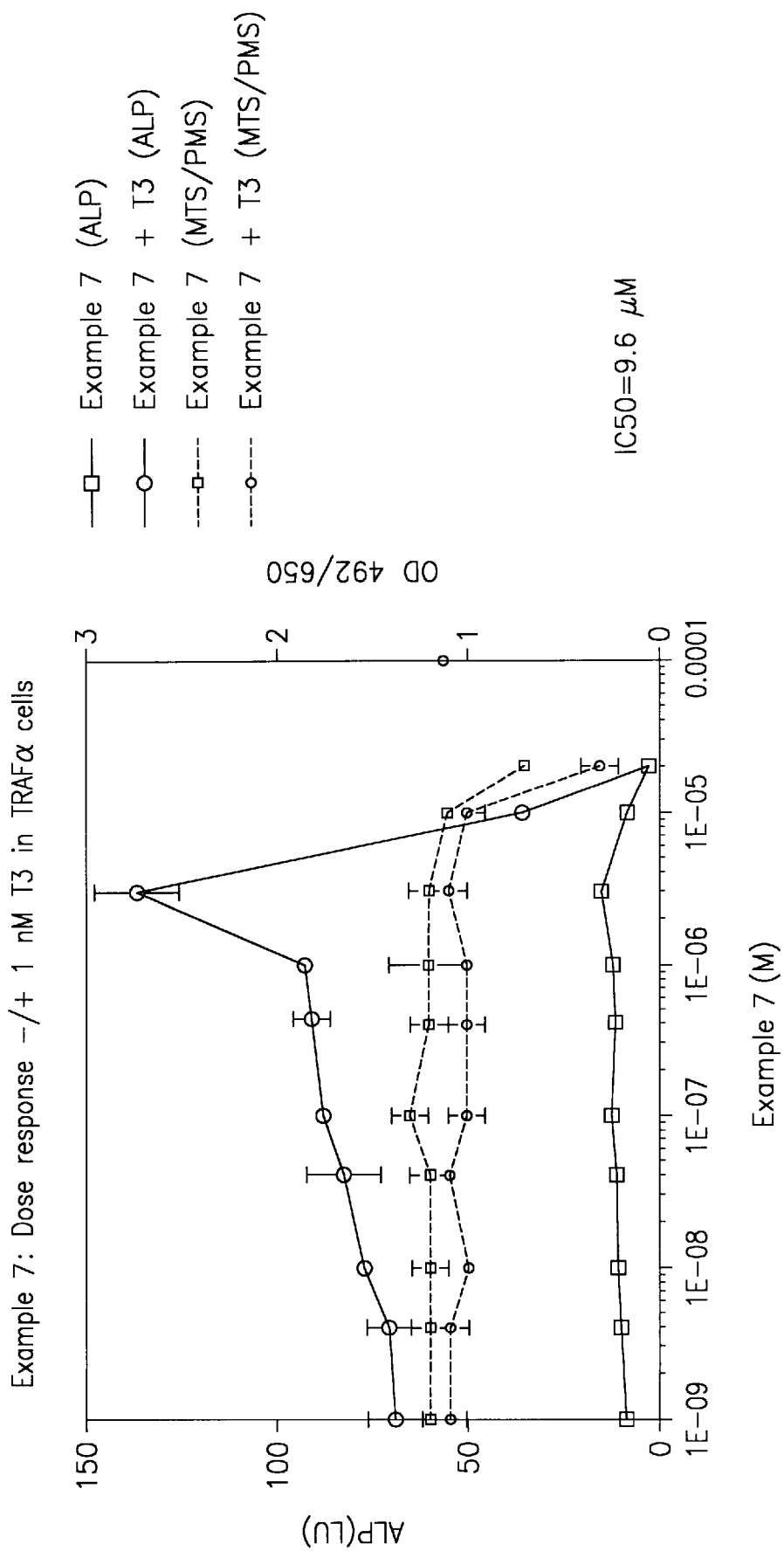
FIG. 8 illustrates the effects of 2-Isopropyl-3-(3,5-diiodo-4-carboxymethoxybenzoyl)-5-(4-methoxybenzamido) benzofuran on TRAF α cells.
Figure 9:
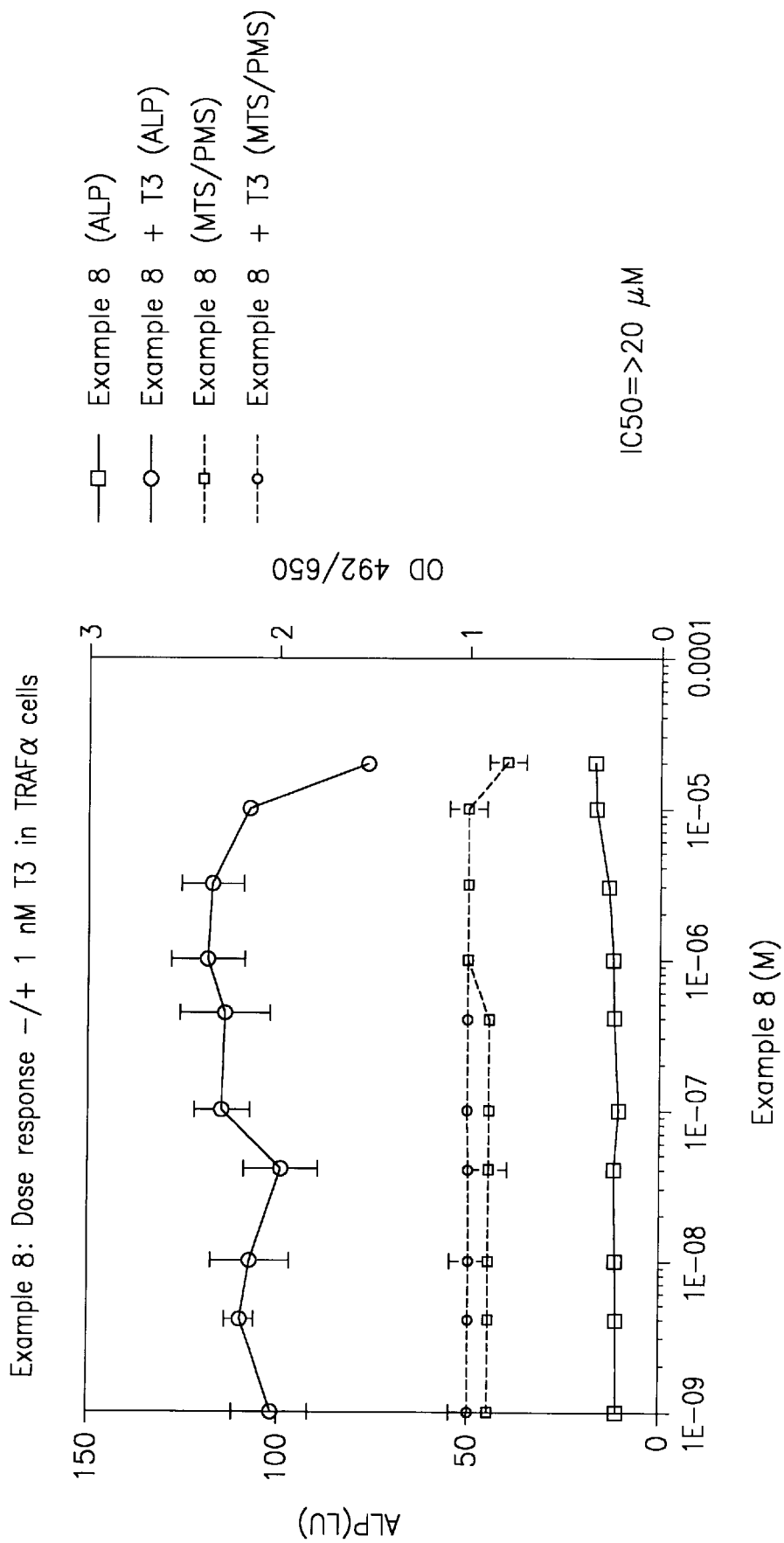
FIG. 9 illustrates the effects of 2-Isopropyl-3-(3,5-diiodo-4-carboxymethoxybenzoyl)-5-(4-hydroxybenzamido)benzofuran on TRAF α cells.
Figure 10:
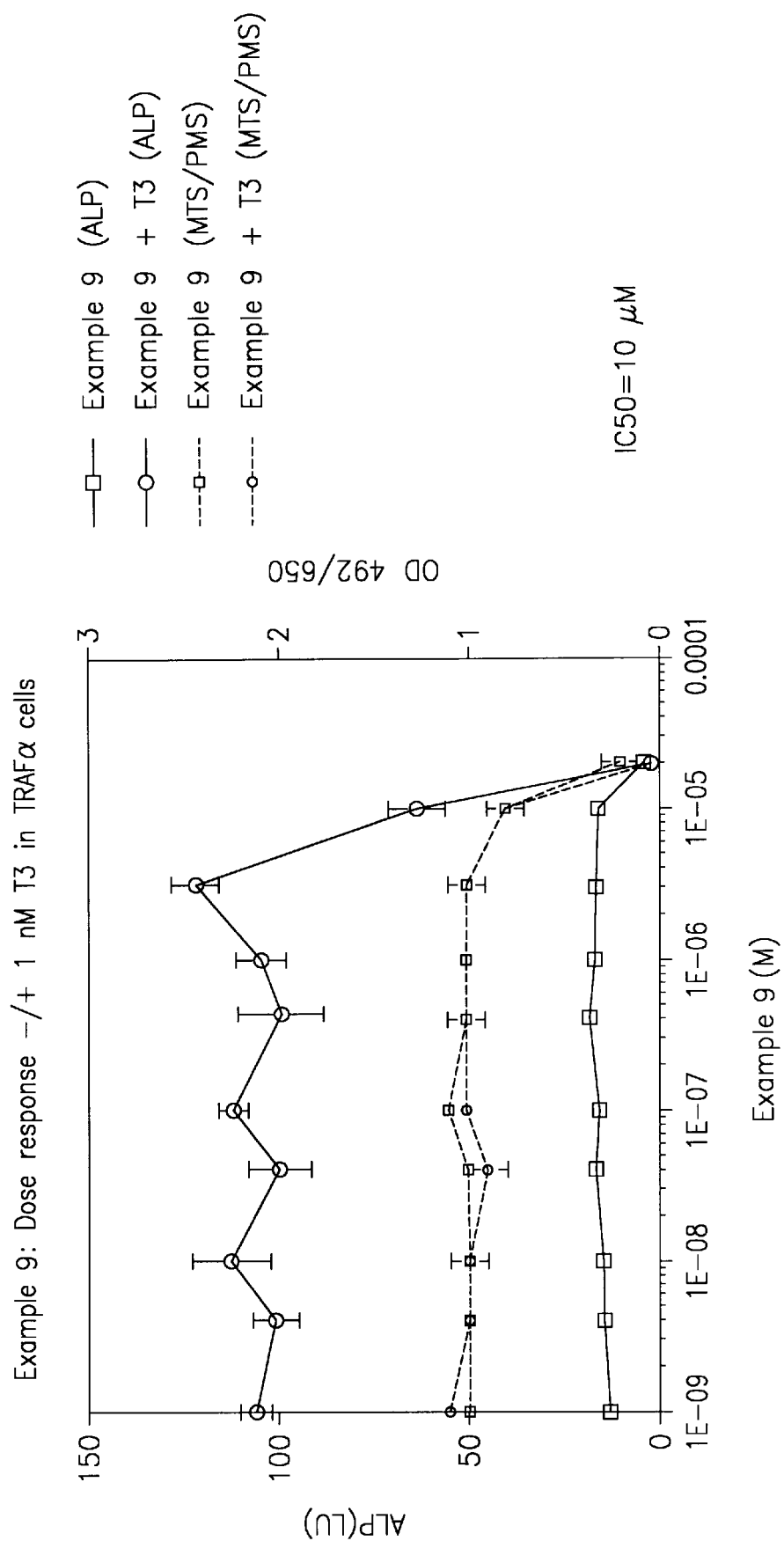
FIG. 10 illustrates the effects of 2-n-Butyl-3-(3,5-diiodo-4-carboxymethoxybenzoyl)-5-(4-fluorobenzamido)benzofuran on TRAF α cells.
Figure 11:
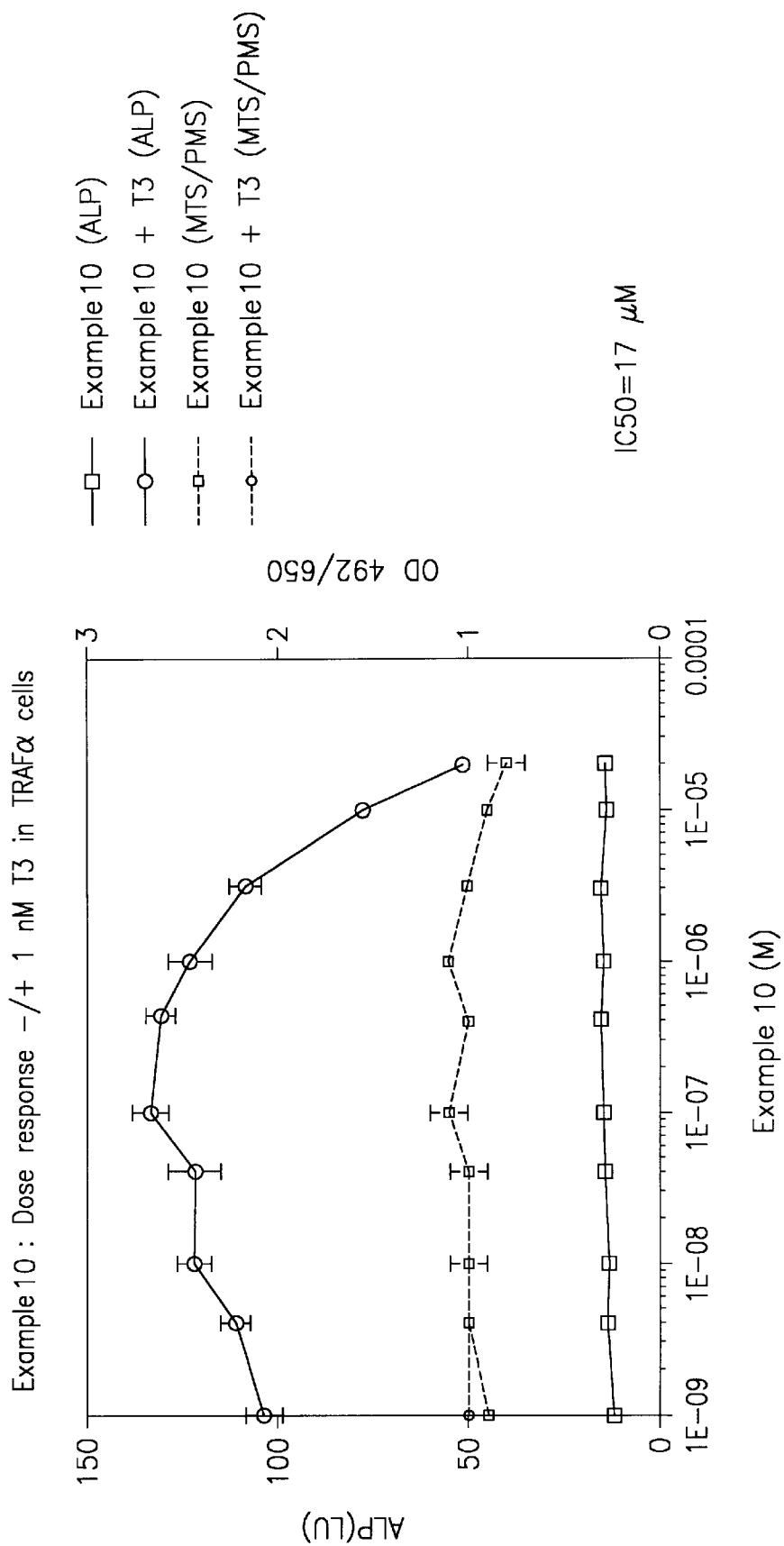
FIG. 11 illustrates the effects of 2-Isopropyl-3-(3,5-diiodo-4-carboxymethoxybenzoyl)-5-(4-nitrobenzamido)benzofuran on TRAF α cells.
Figure 12:
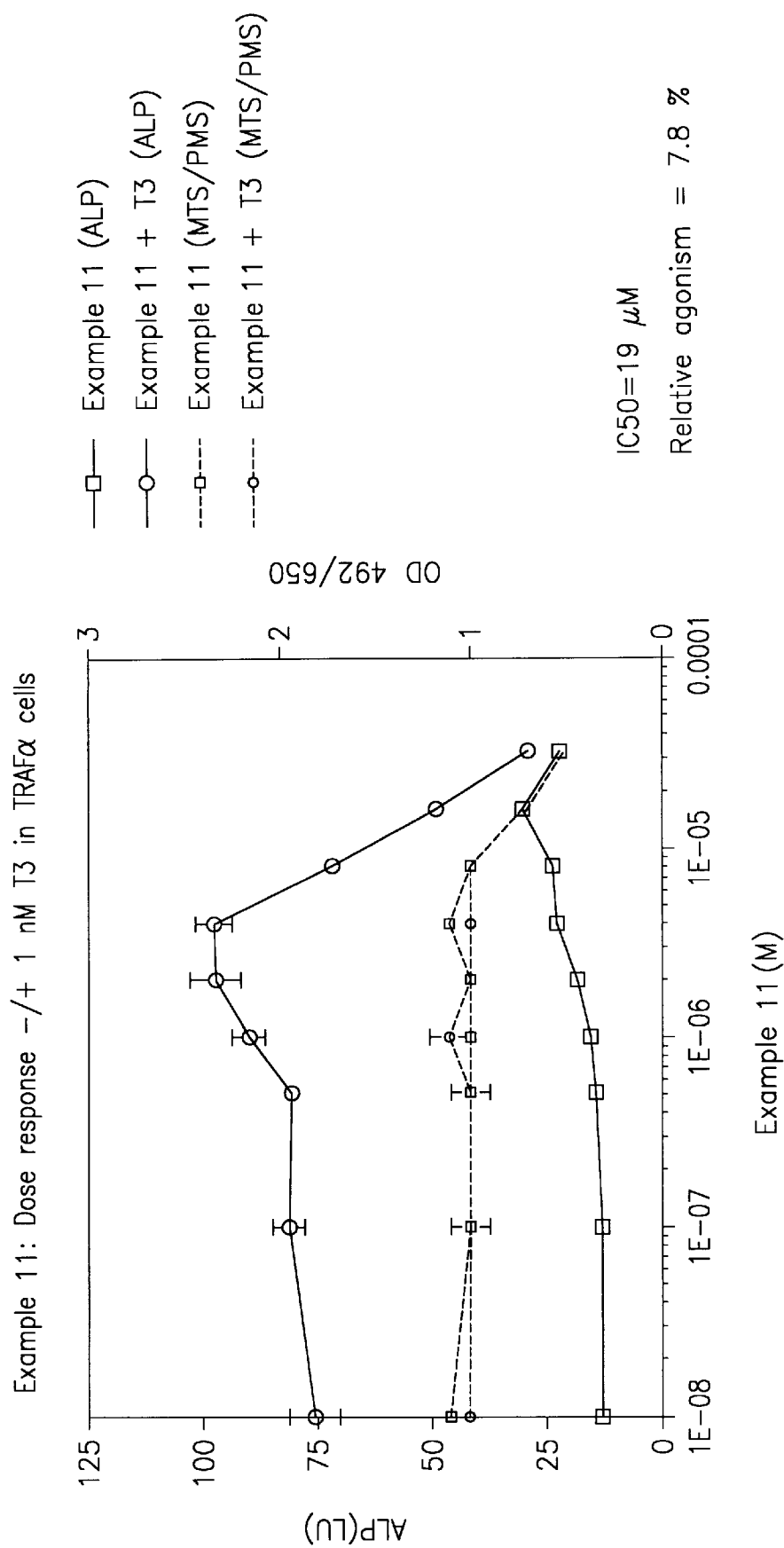
FIG. 12 illustrates the effects of 2-n-Butyl-3-(3,5-diiodo-4-carboxymethoxybenzoyl)-5-(4-methoxyphenylureido)benzofuran on TRAF α cells.
Figure 13:
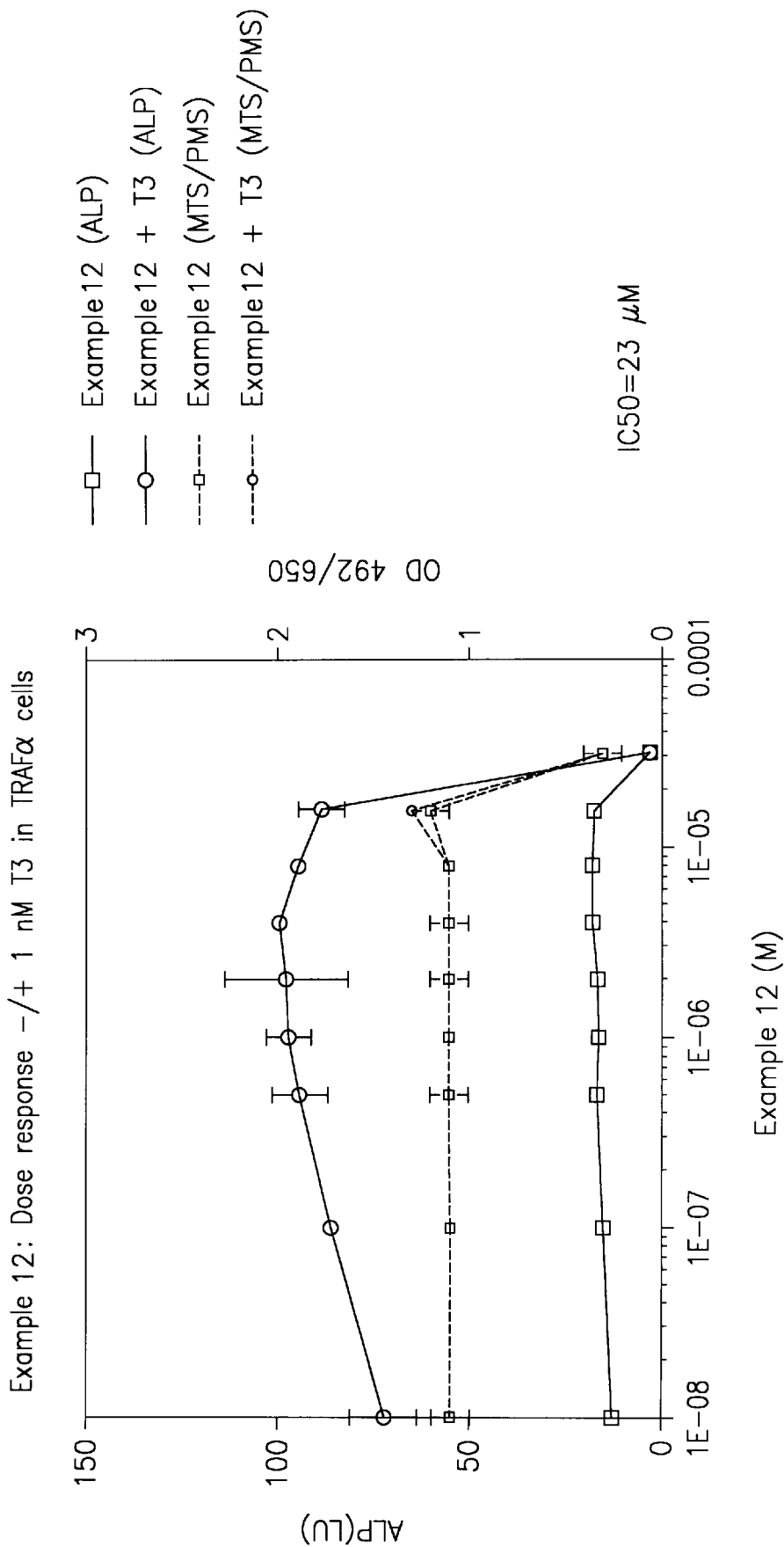
FIG. 13 illustrates the effects of 2-n-Butyl-3-(3,5-diiodo-4-carboxymethoxybenzoyl)-5-(4-hydroxyphenylureido)benzofuran on TRAF α cells.
Figure 14:
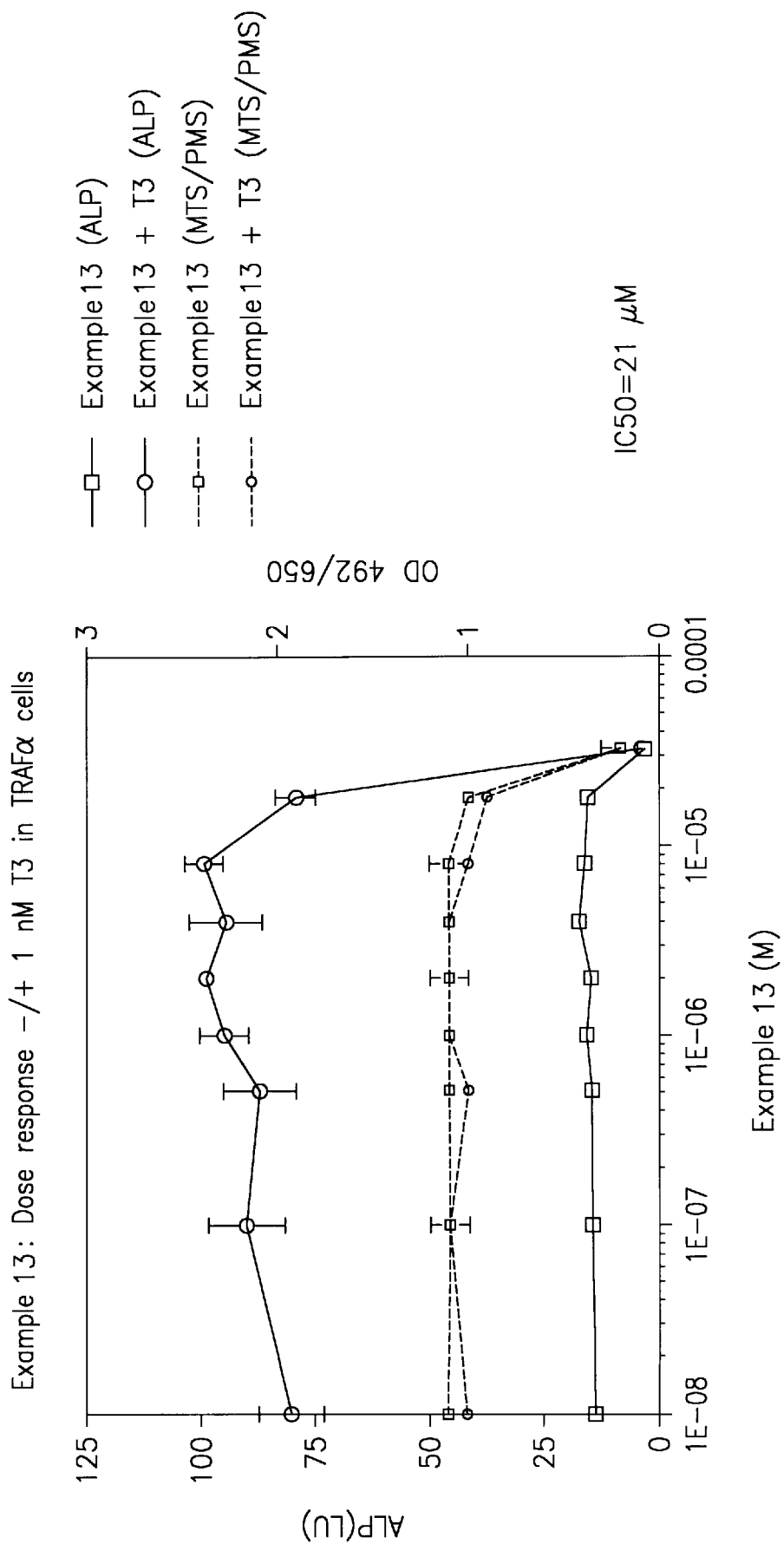
FIG. 14 illustrates the effects of 2-n-Butyl-3-(3,5-dibromo-4-carboxymethoxybenzoyl)-5-(4-hydroxybenzamido)benzofuran on TRAF α cells.
Figure 15:
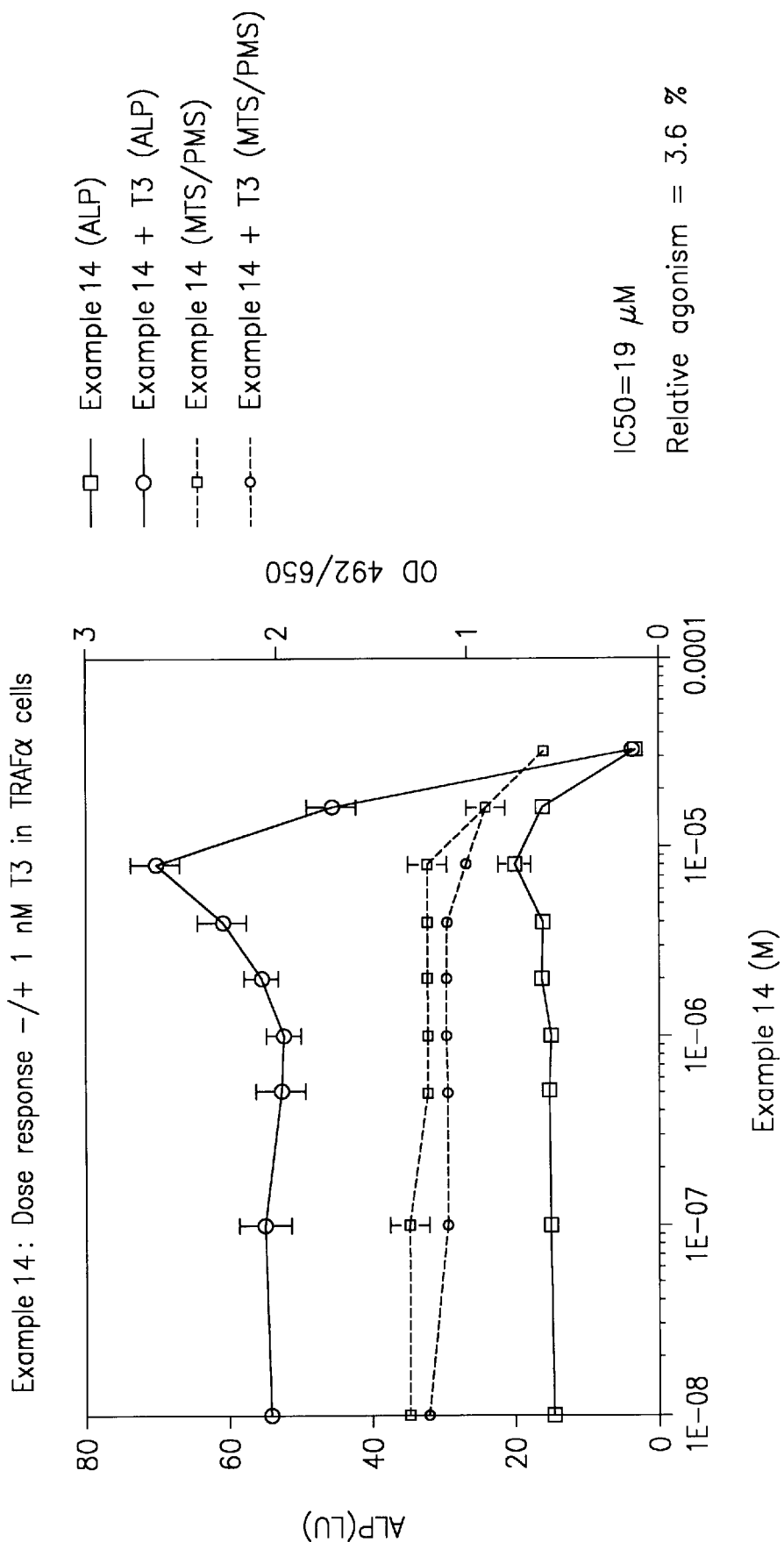
FIG. 15 illustrates the effects of 2-Isopropyl-3-(3,5-dibromo-4-carboxymethoxybenzoyl)-5-(4-methoxybenzamido)benzofuran on TRAF α cells.
Figure 16:
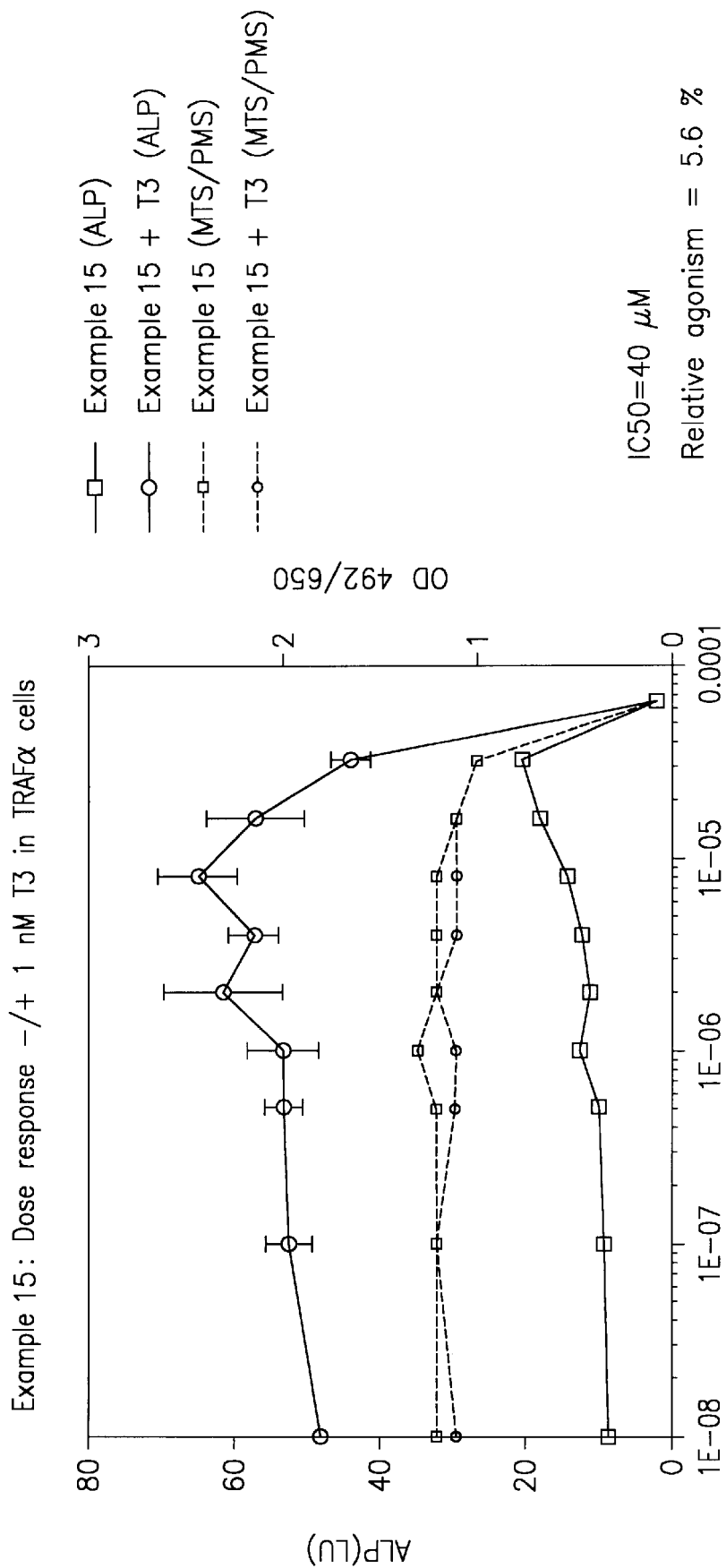
FIG. 16 illustrates the effects of 2-Isopropyl-3-(3,5-dibromo-4-carboxymethoxybenzoyl)-5-(4-hydroxybenzamido)benzofuran on TRAF α cells.
Figure 17:
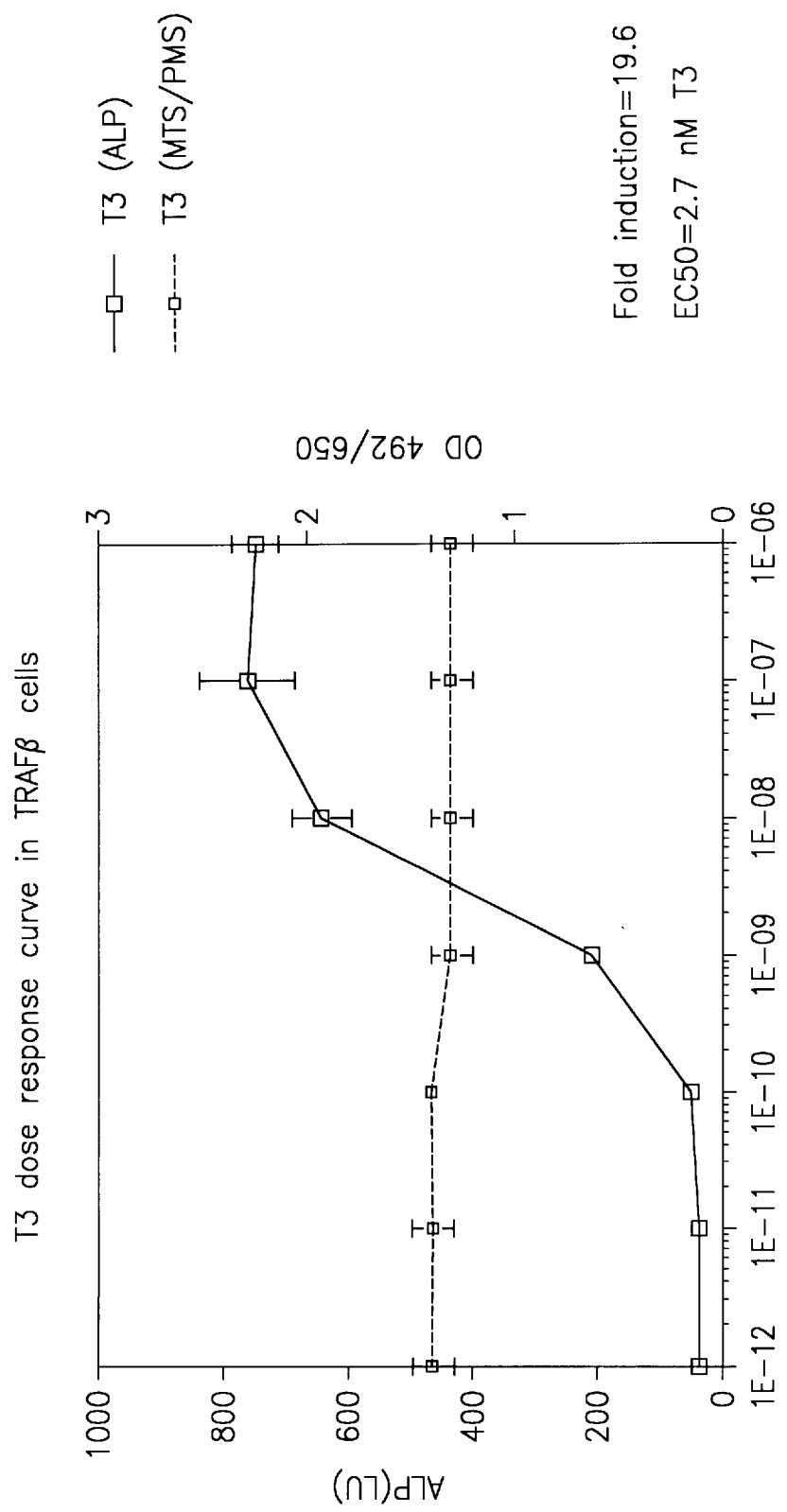
FIG. 17 is a T3 dose response curve in TRAF β cells.
Figure 18:
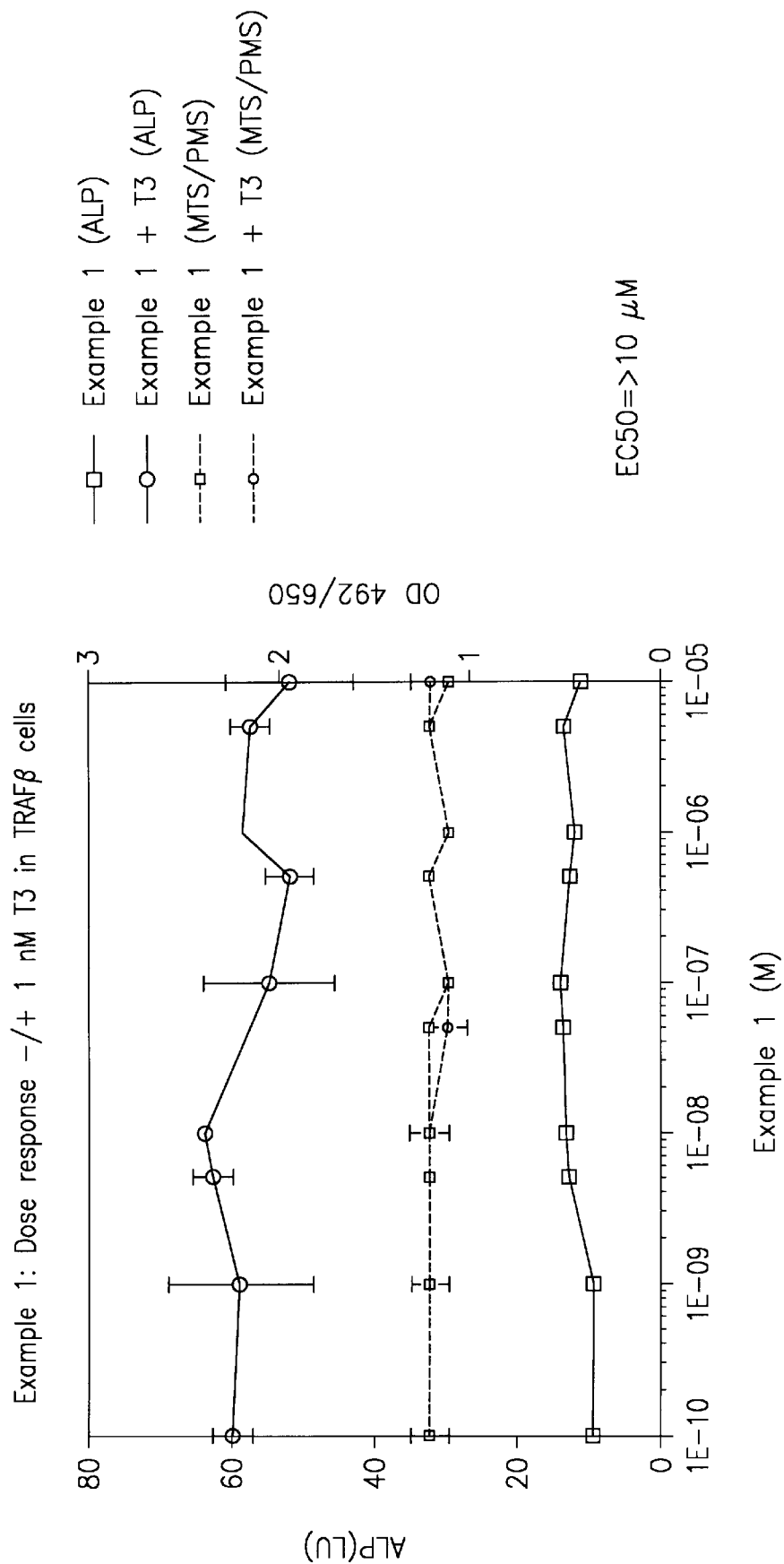
FIG. 18 illustrates the effects of 2-n-Butyl-3(3,5-diiodo-4-carboxymethoxybenzoyl)-5-trifluoromethylsulphonamidobenzofuran in TRAF β cells.
Figure 19:
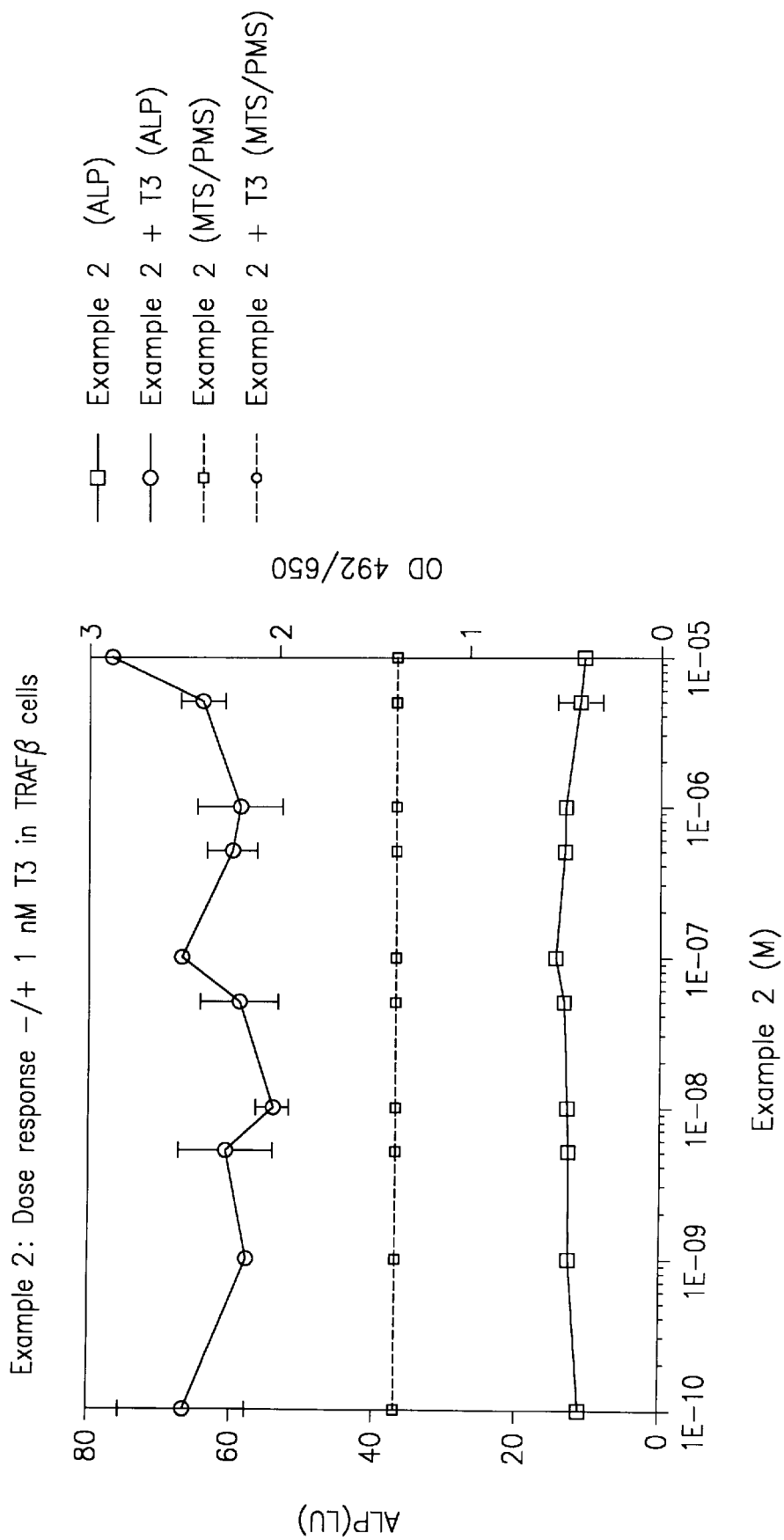
FIG. 19 illustrates the effects of 2-n-butyl-3,5-diiodo-4-carboxymethoxybenzoyl)-5-isopropylamidobenzofuran on TRAF β cells.
Figure 20:
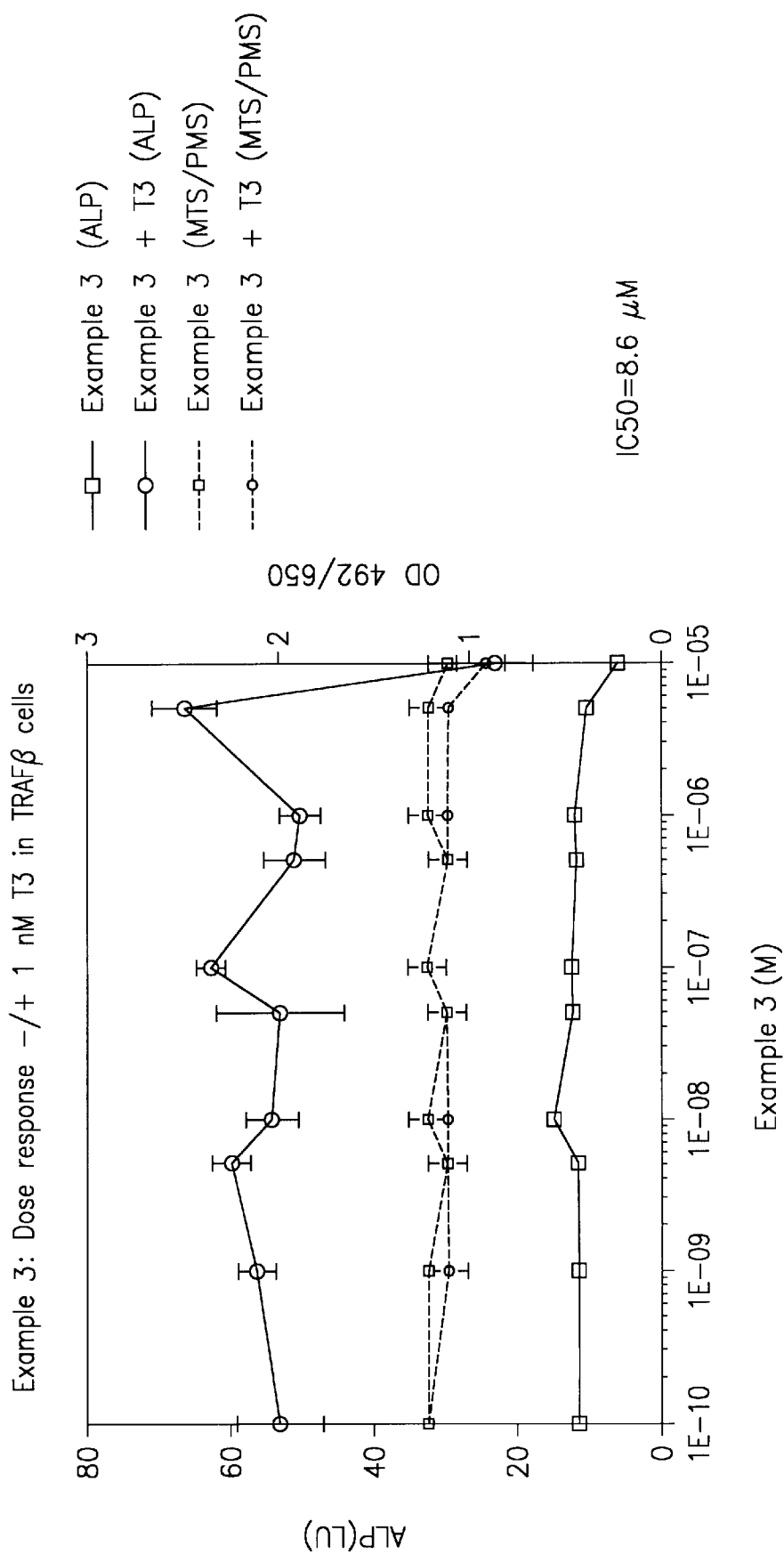
FIG. 20 illustrates the effects of 2-n-Butyl-3-(3,5-diiodo-4-carboxymethoxybenzoyl)-5-(4-methoxybenzamido)benzofuran on TRAF β cells.
Figure 21:
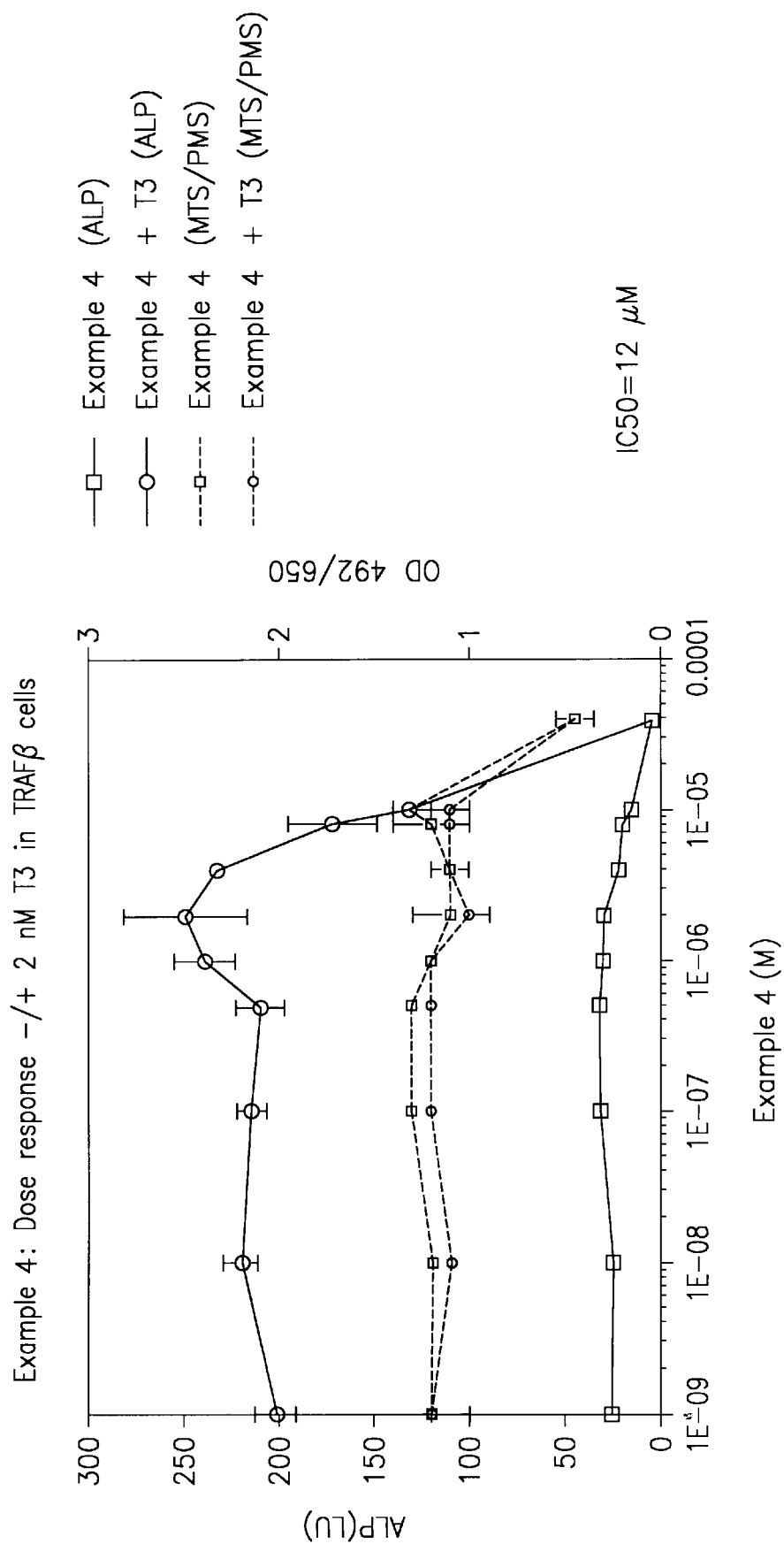
FIG. 21 illustrates the effects of 2-n-Butyl-3-(3,5-diiodo-4-carboxymethoxybenzoyl)-5-(4-hydroxybenzamido)benzofuran on TRAF β cells.
Figure 22:
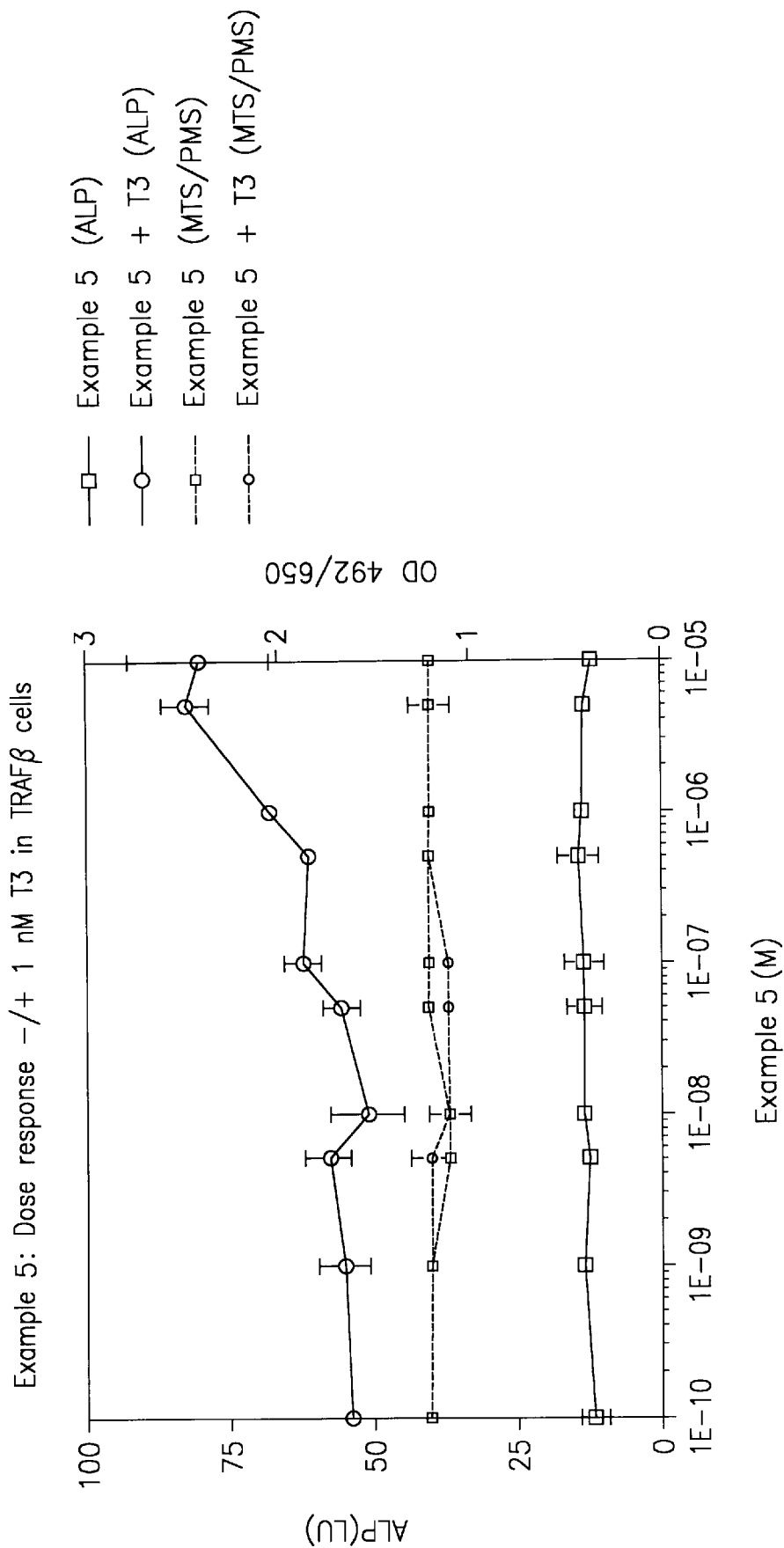
FIG. 22 illustrates the effects of 2-Isopropyl-3-(3,5-diiodo-4-carboxymethoxybenzyl)-5-trifluoromethylsulphonamidobenzofuran on TRAF β cells.
Figure 23:
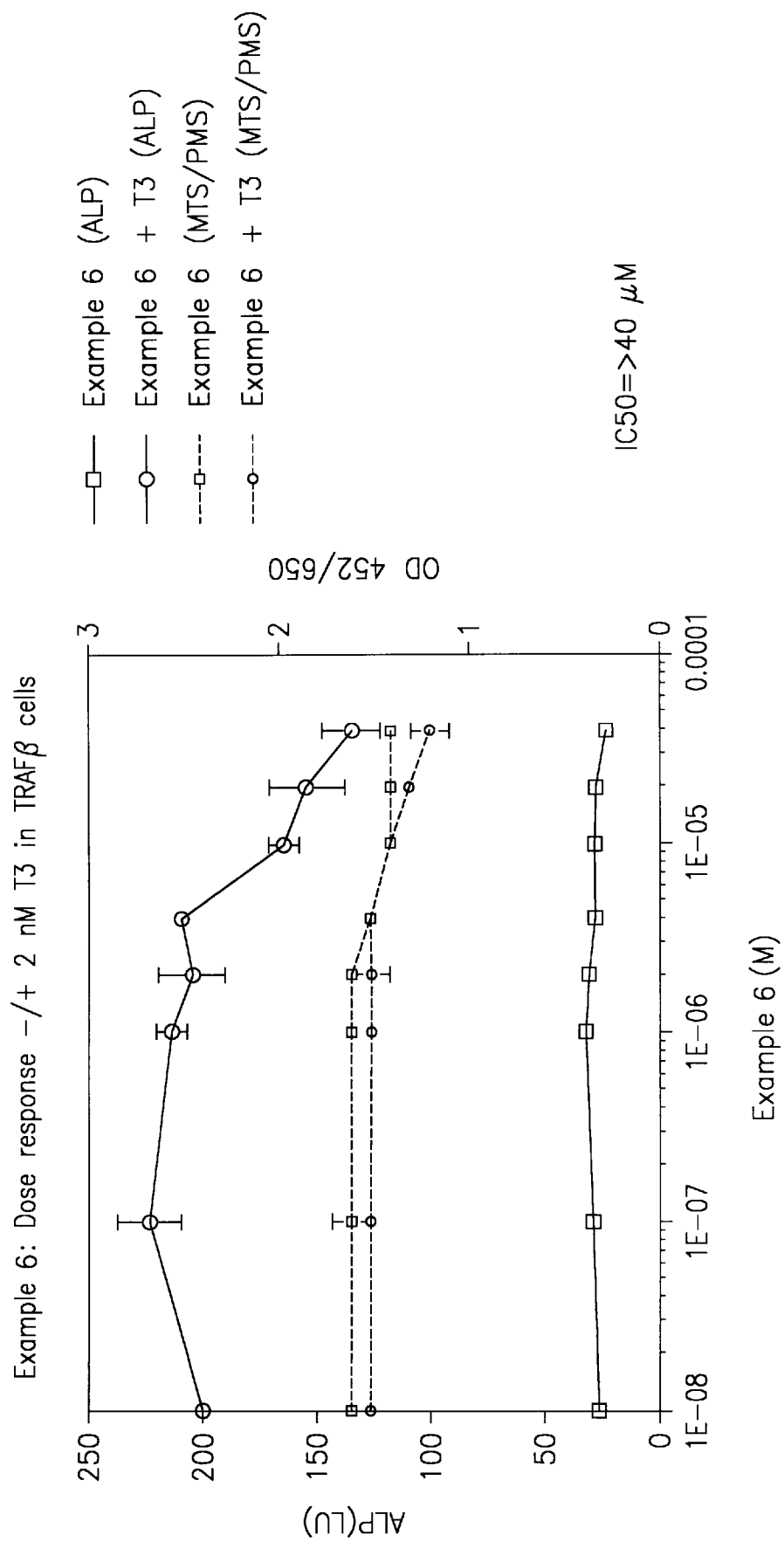
FIG. 23 illustrates the effects of 2-isopropyl-3-(3,5-diiodo-4-carboxymethoxybenzoyl)-5-trifluoromethylsulphonamidobenzofuran on TRAF β cells.
Figure 24:
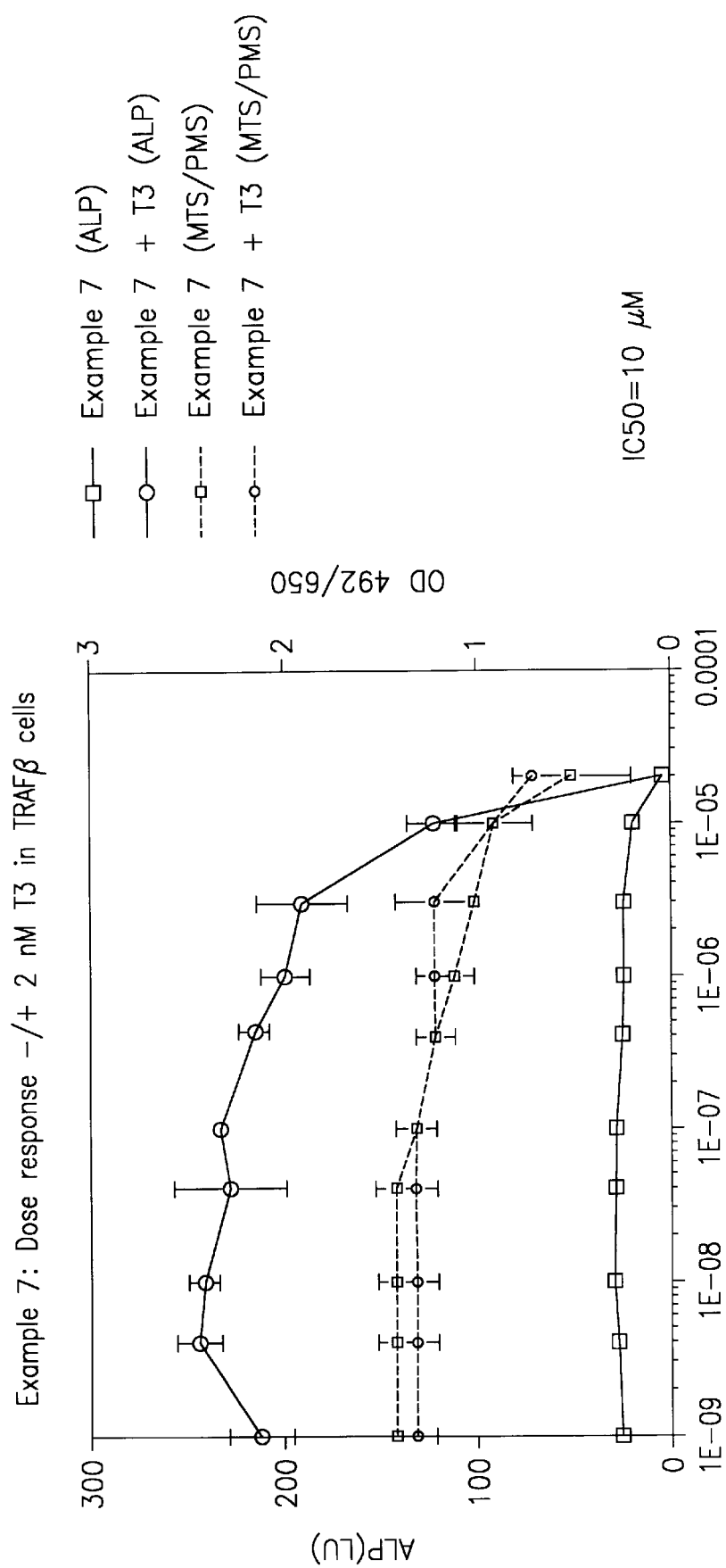
FIG. 24 illustrates the effects of 2-Isopropyl-3-(3,5-diiodo-4-carboxymethoxybenzoyl)-5-(4-methoxybenzamido)benzofuran on TRAF β cells.
Figure 25:
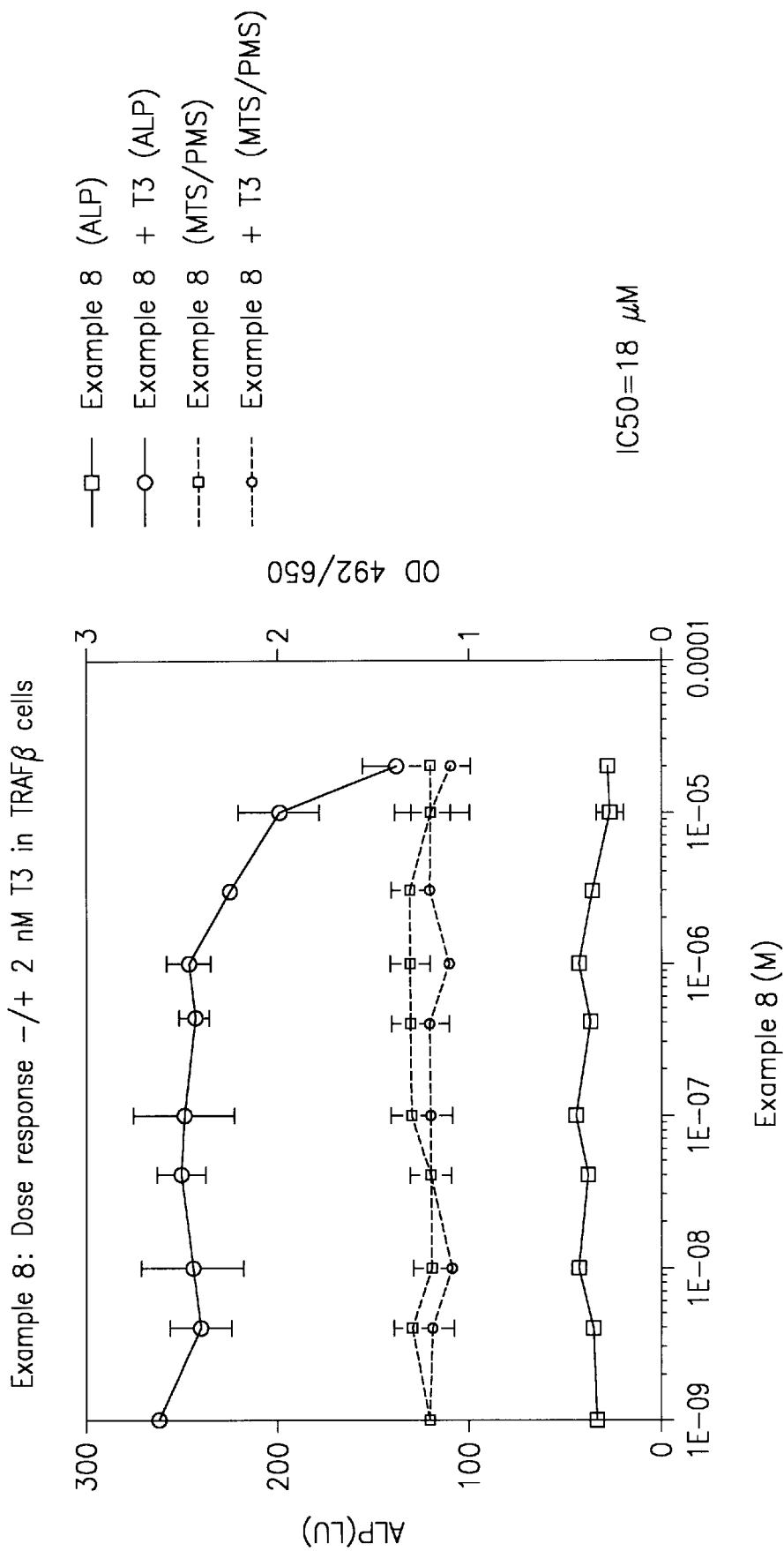
FIG. 25 illustrates the effects of 2-Isopropyl-3-(3,5-diiodo-4-carboxymethoxybenzoyl)-5-(4-hydroxybenzamido)benzofuran on TRAF β cells.
Figure 26:
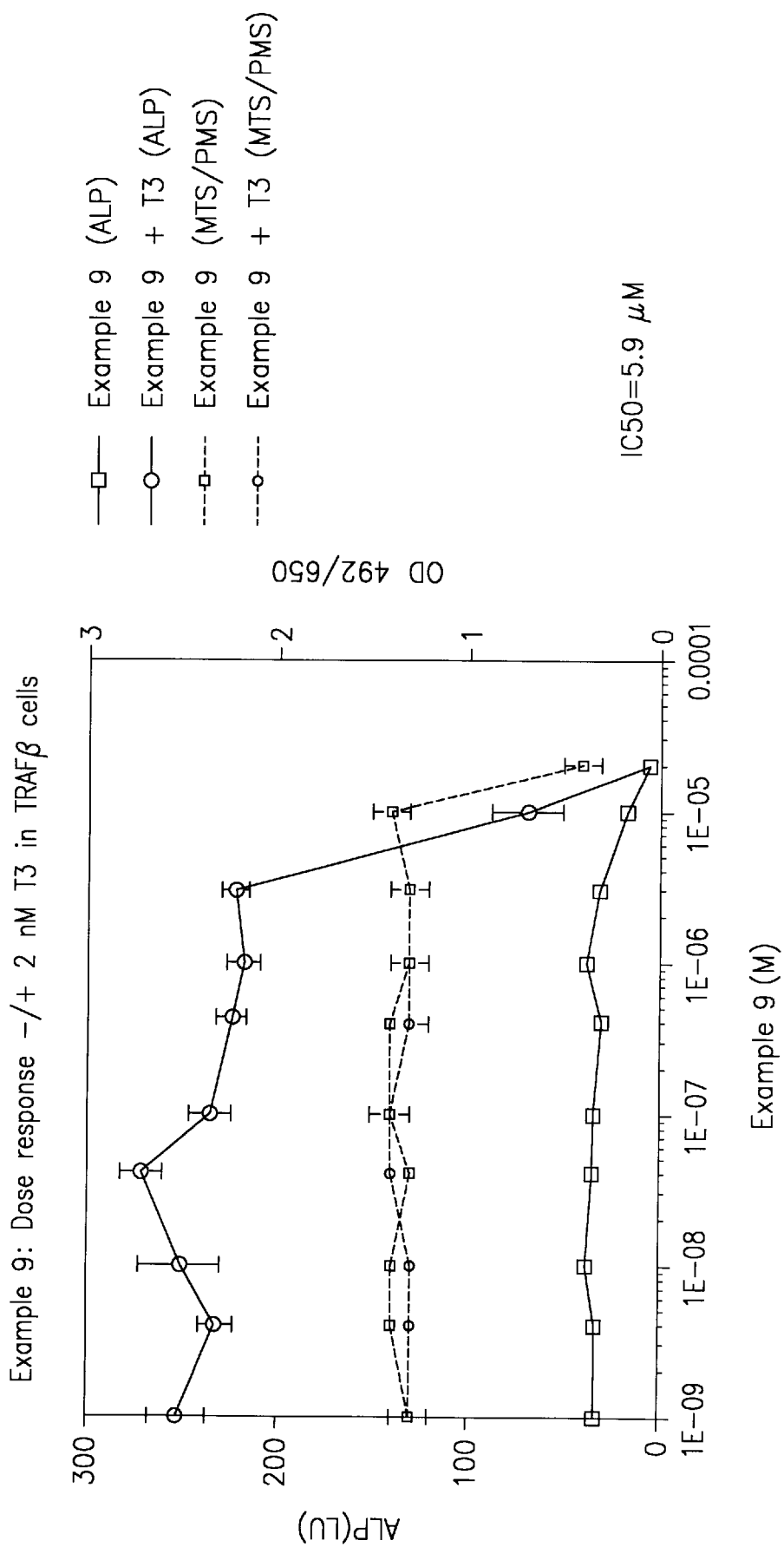
FIG. 26 illustrates the effects of 2-n-Butyl-3-(3,5-diiodo-4-carboxymethoxybenzoyl)-5-(4-fluorobenzamido)benzofuran on TRAF β cells.
Figure 27:
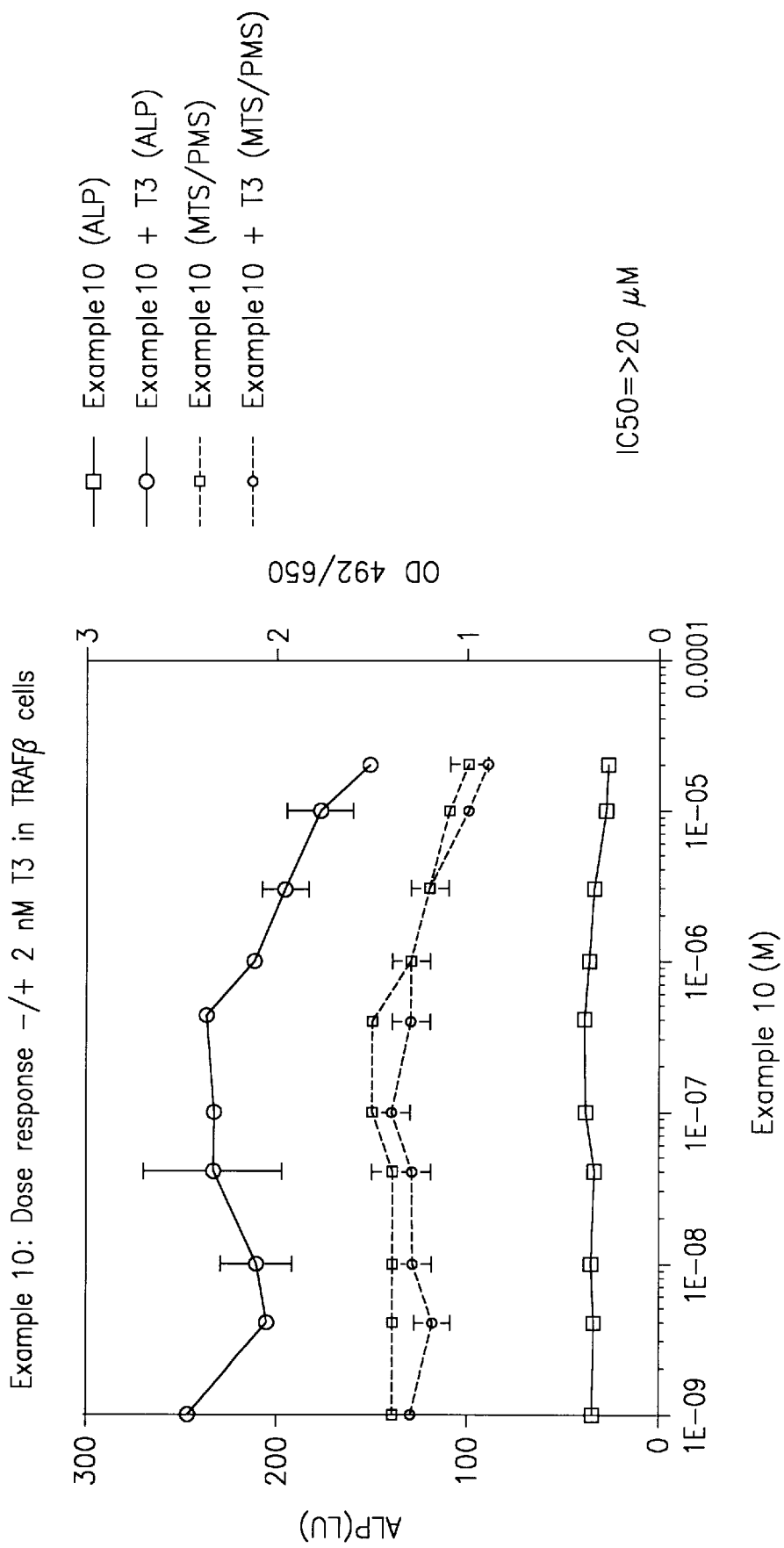
FIG. 27 illustrates the effects of 2-Isopropyl-3-(3,5-diiodo-4-carboxymethoxybenzoyl)-5-(4-nitrobenzamido)benzofuran on TRAF β cells.
Figure 28:
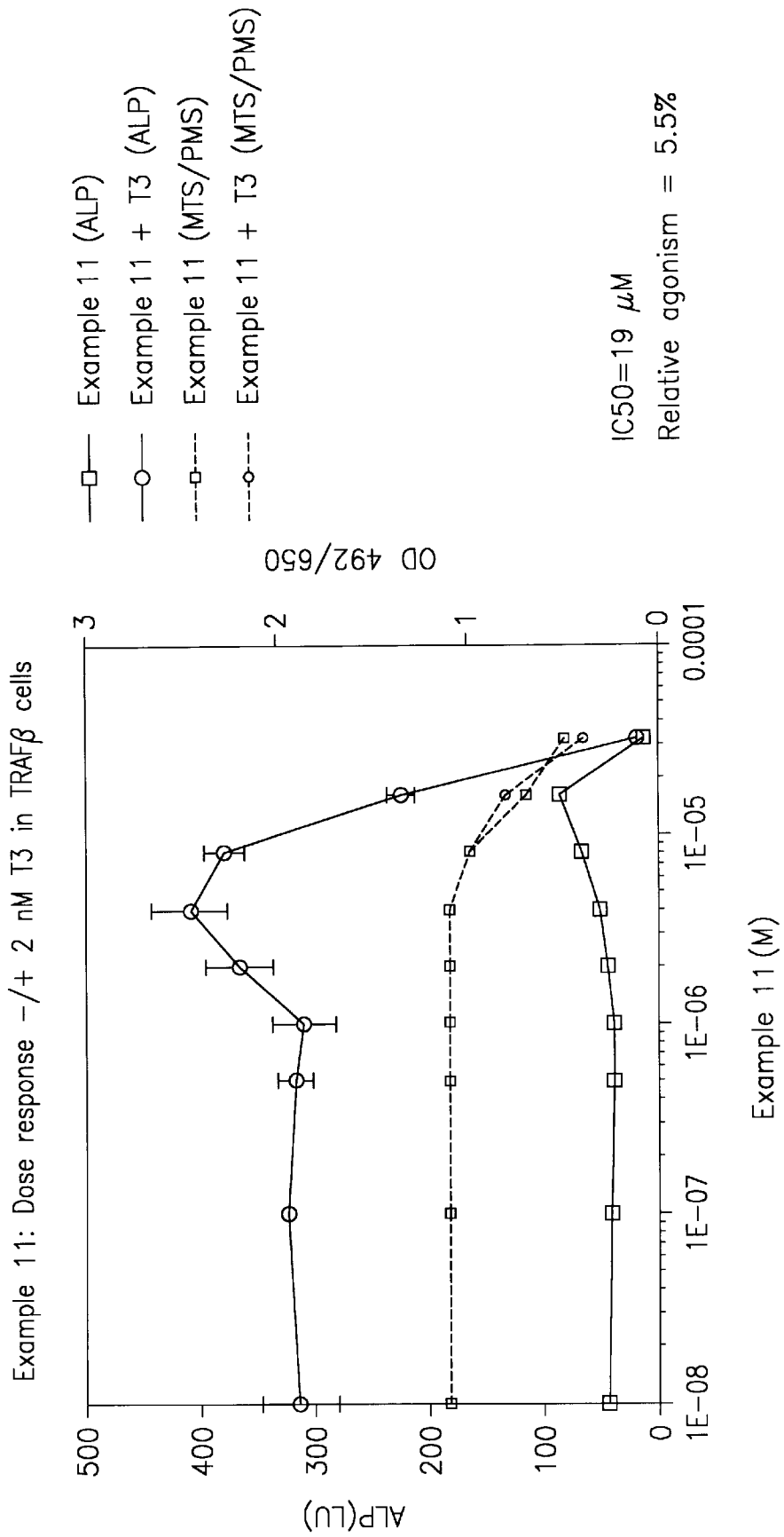
FIG. 28 illustrates the effects of 2-n-Butyl-3-(3,5-diiodo-4-carboxymethoxybenzoyl)-5-(4-methoxyphenylureido)benzofuran on TRAF β cells.
Figure 29:
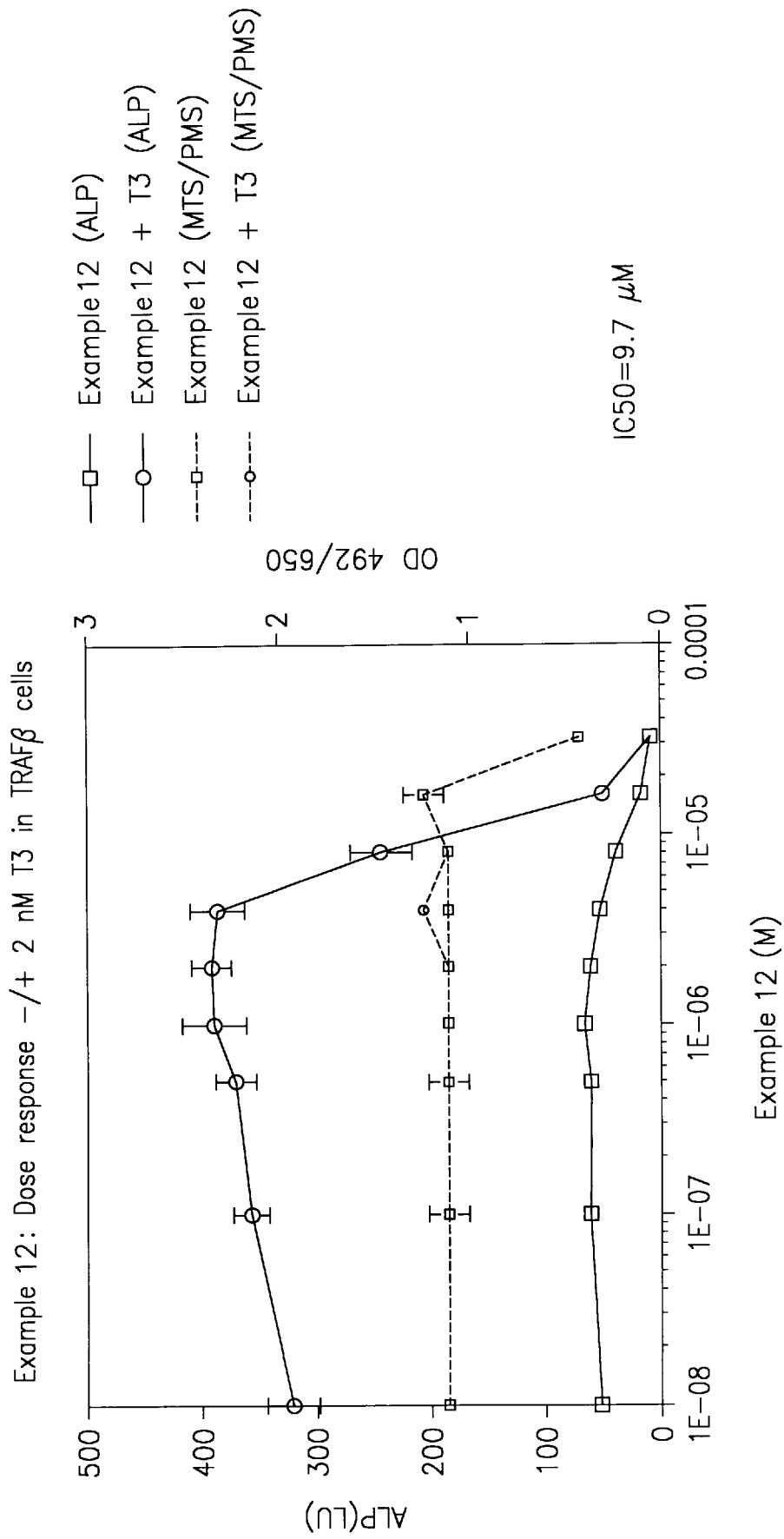
FIG. 29 illustrates the effects of 2-n-Butyl-3-(3,5-diiodo-4-carboxymethoxybenzoyl)-5-(4-hydroxyphenylureido)benzofuran on TRAF β cells.
Figure 30:
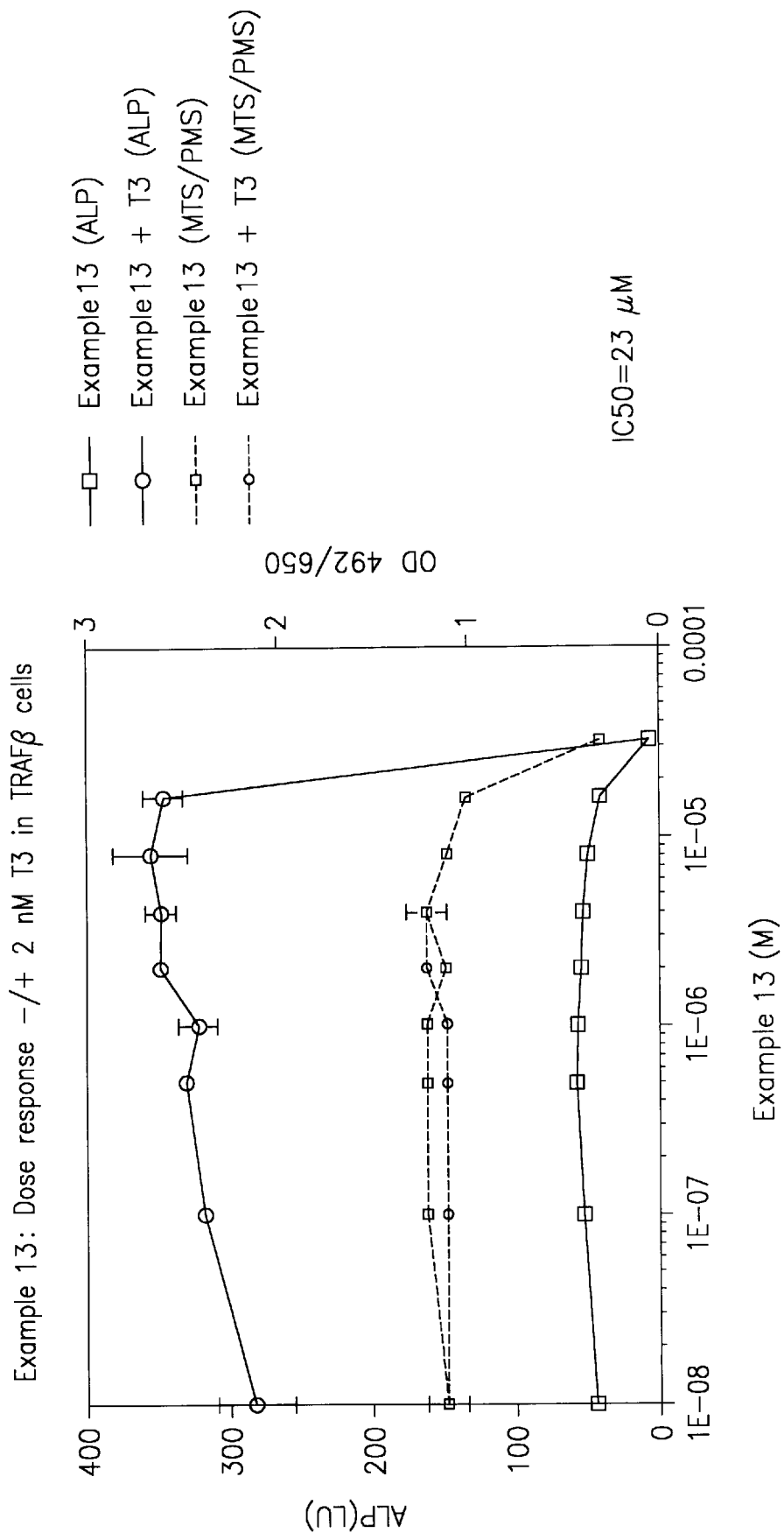
FIG. 30 illustrates the effects of 2-n-Butyl-3-(3,5-dibromo-4-carboxymethoxybenzoyl)-5-(4-hydroxybenzamido)benzofuran on TRAF β cells.
Figure 31:
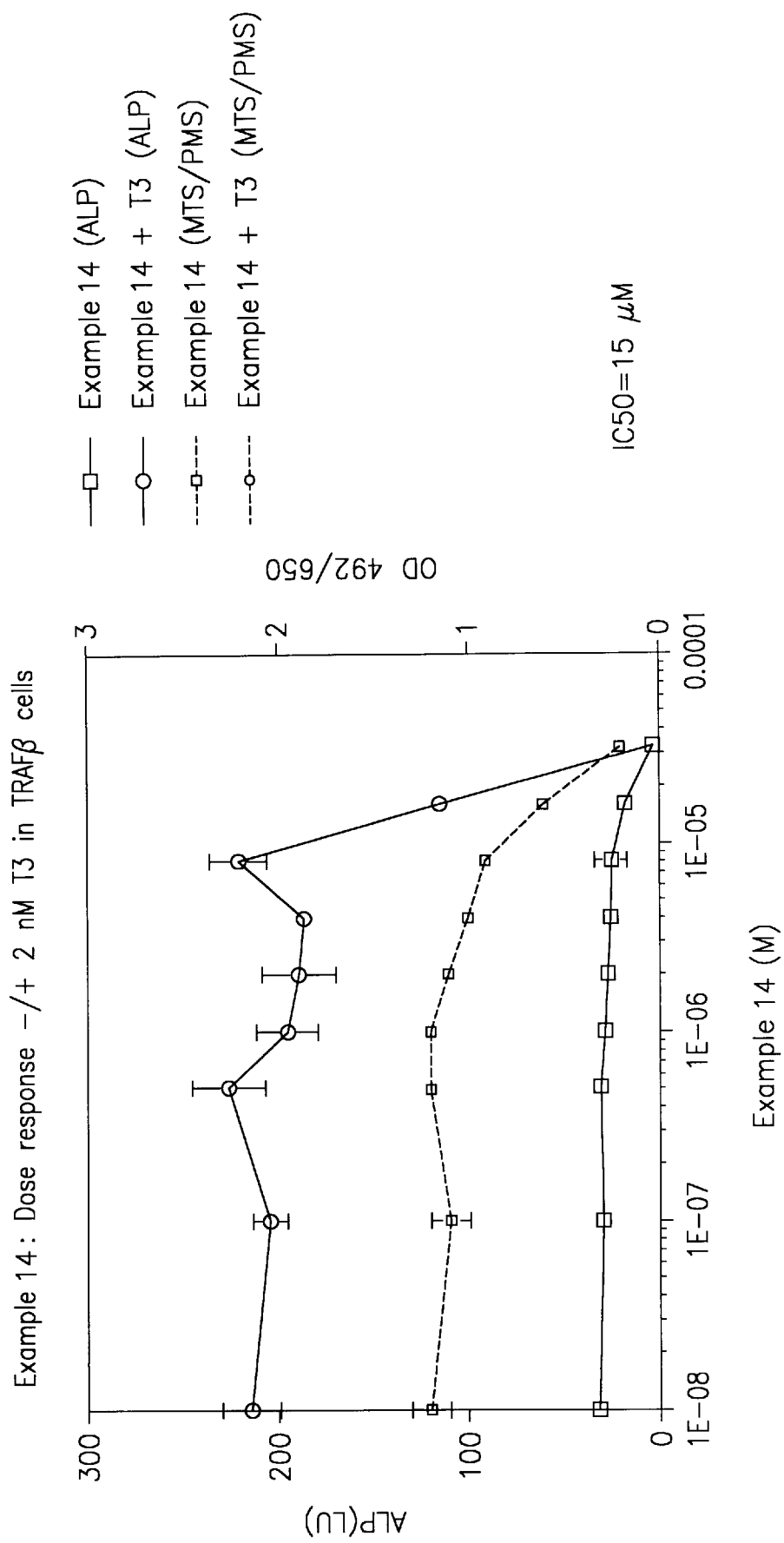
FIG. 31 illustrates the effects of 2-Isopropyl-3-(3,5-dibromo-4-carboxymethoxybenzoyl)-5-(4-methoxybenzamido)benzofuran on TRAF β cells.
Figure 32:
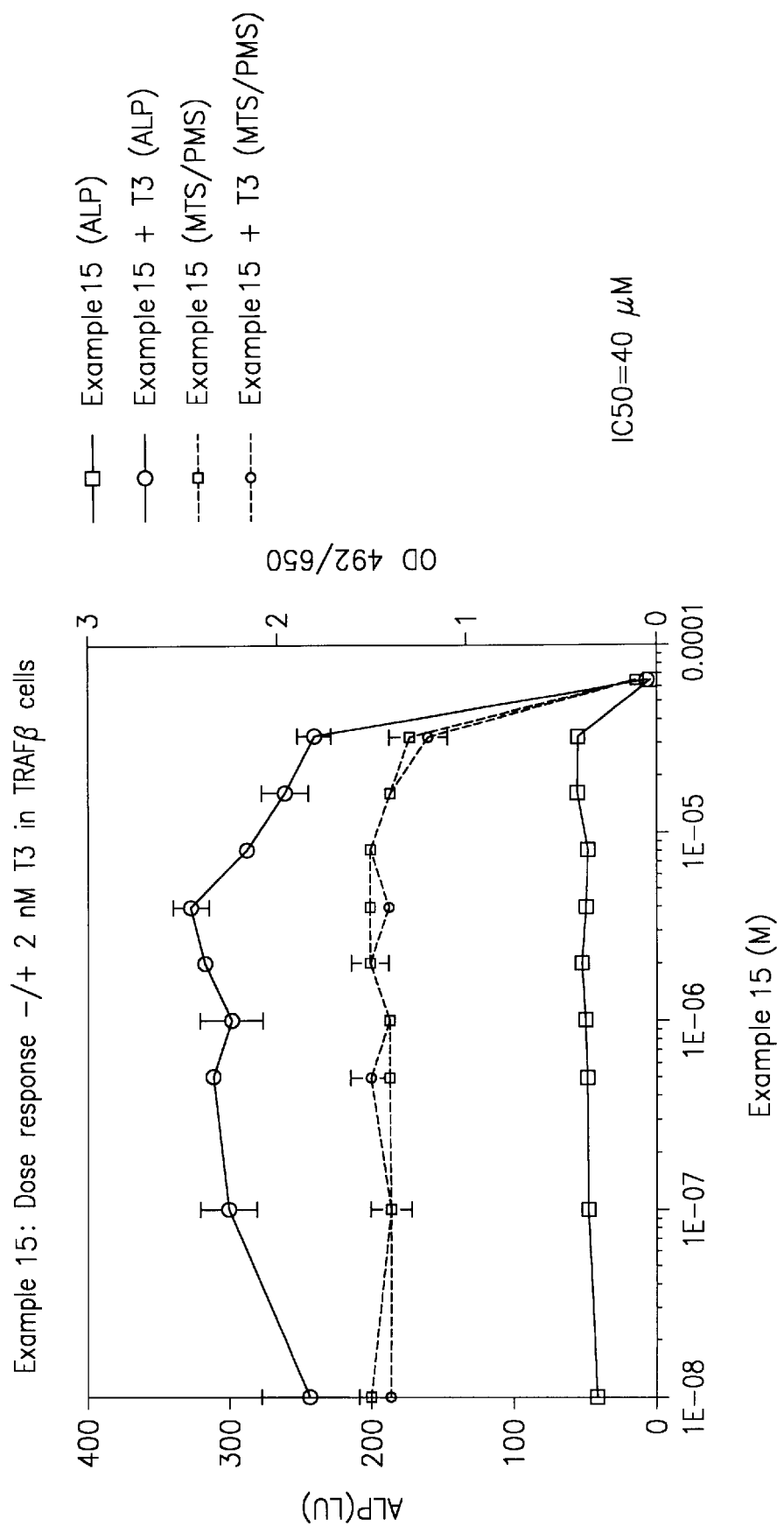
FIG. 32 illustrates the effects of 2-Isopropyl-3-(3,5-dibromo-4-carboxymethoxybenzoyl)-5-(4-hydroxybenzamido)benzofuran on TRAF β cells.
Figure 33:
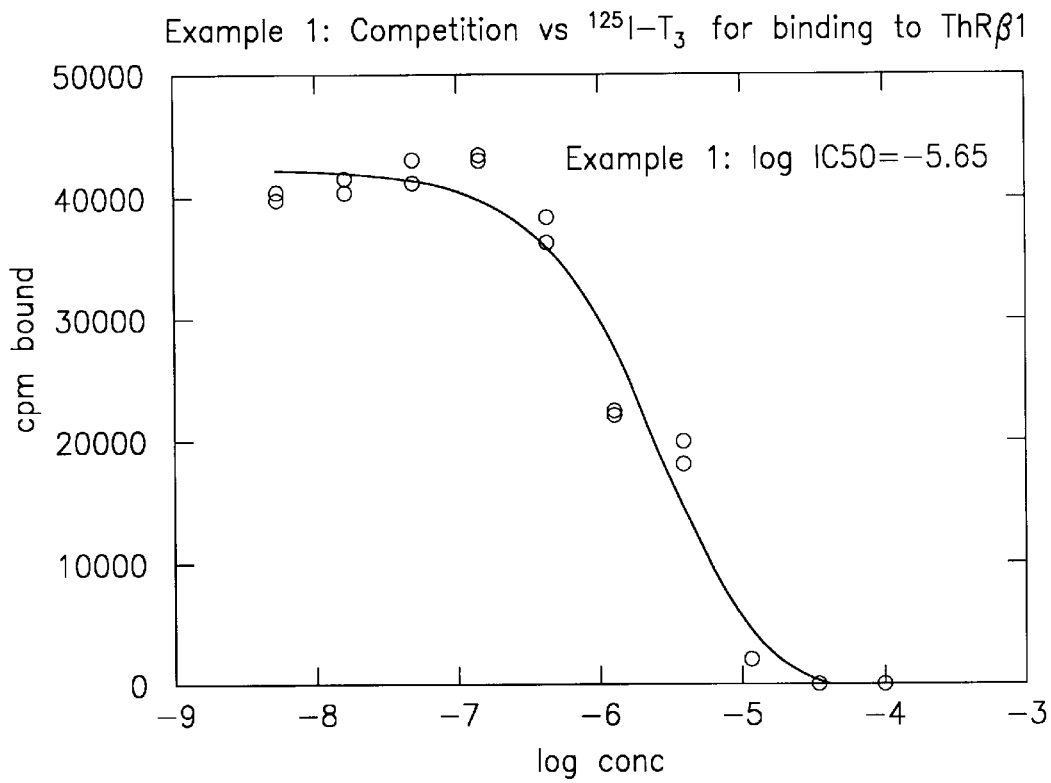
FIG. 33 illustrates competition between 2-n-Butyl-3(3,5-diiodo-4-carboxymethoxybenzoyl)-5-trifluoromethylsulphonamidobenzofuran cpd and $^{125}$-T$_3$ for binding to ThRβ1.
Figure 34:
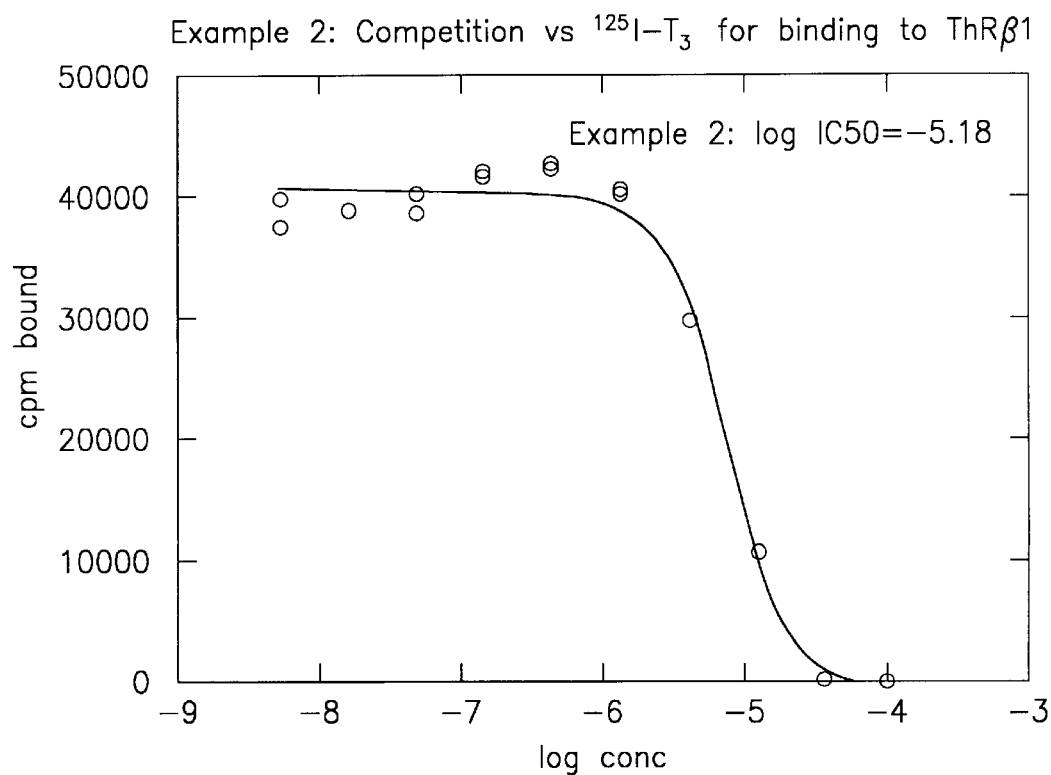
FIG. 34 illustrates competition between 2-n-butyl-3,5-diiodo-4-carboxymethoxybenzoyl)-5-isopropylamidobenzofuran cpd and $^{125}$I-T$_3$ for binding to ThRβ1.
Figure 35:
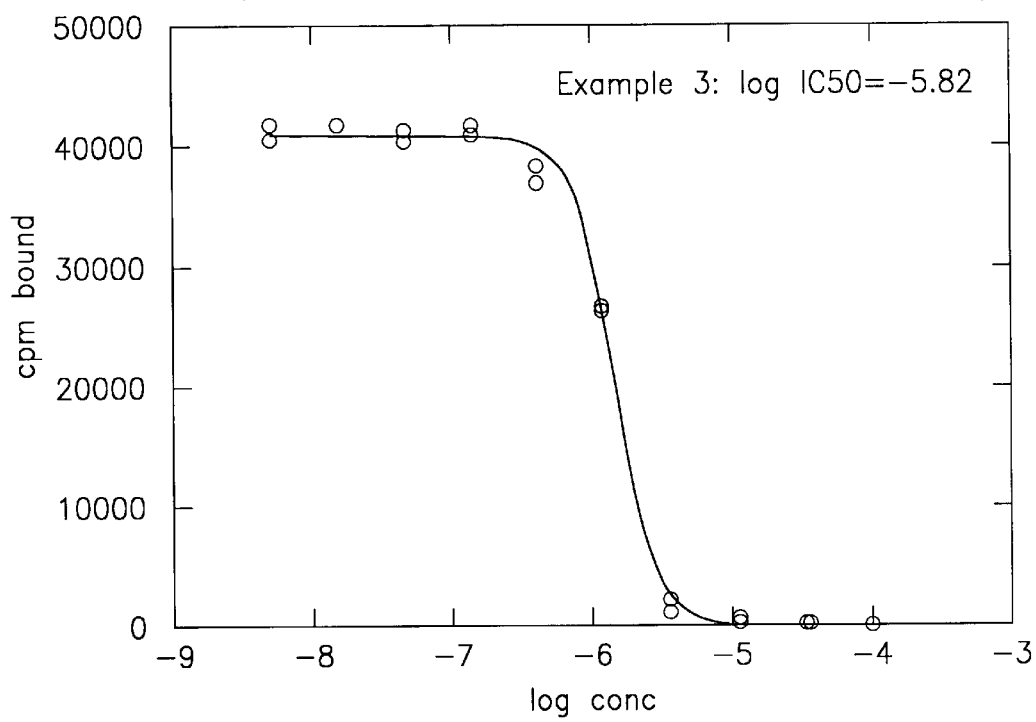
FIG. 35 illustrates competition between 2-n-Butyl-3-(3,5-diiodo-4-carboxymethoxybenzoyl)-5-(4-methoxybenzamido)benzofuran cpd and $^{125}$I-T$_3$ for binding to ThR β1.
Figure 36:
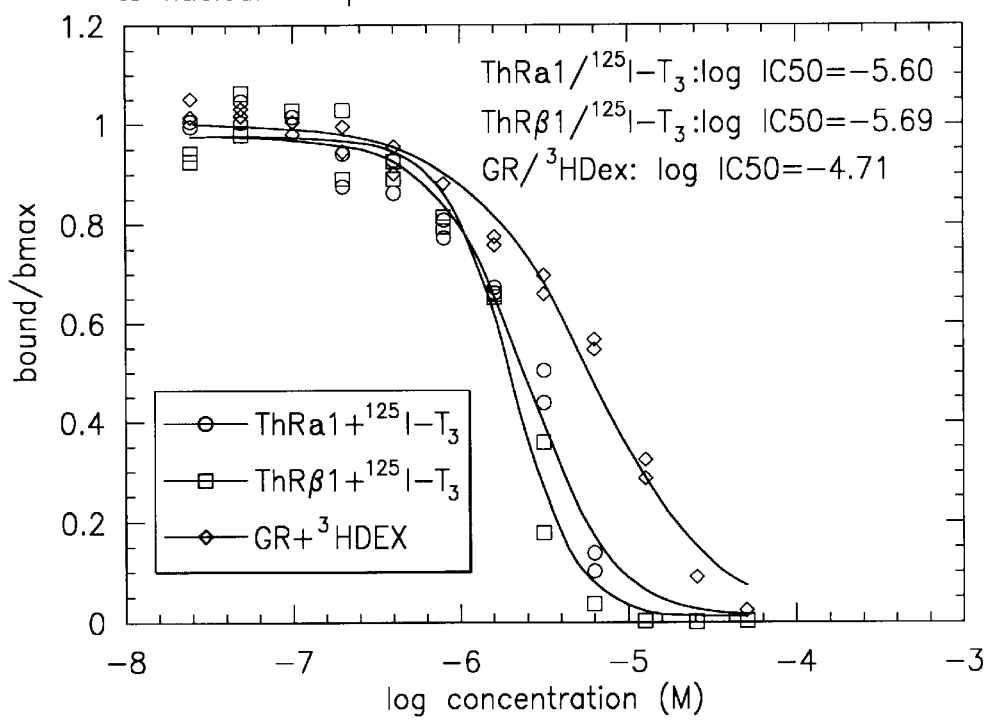
FIG. 36 illustrates competition between 2-n-Butyl-3-(3,5-diiodo-4-carboxymethoxybenzoyl)-5-(4-methoxybenzamido)benzofuran and labelled hormones for binding to nuclear receptors.
Figure 37:
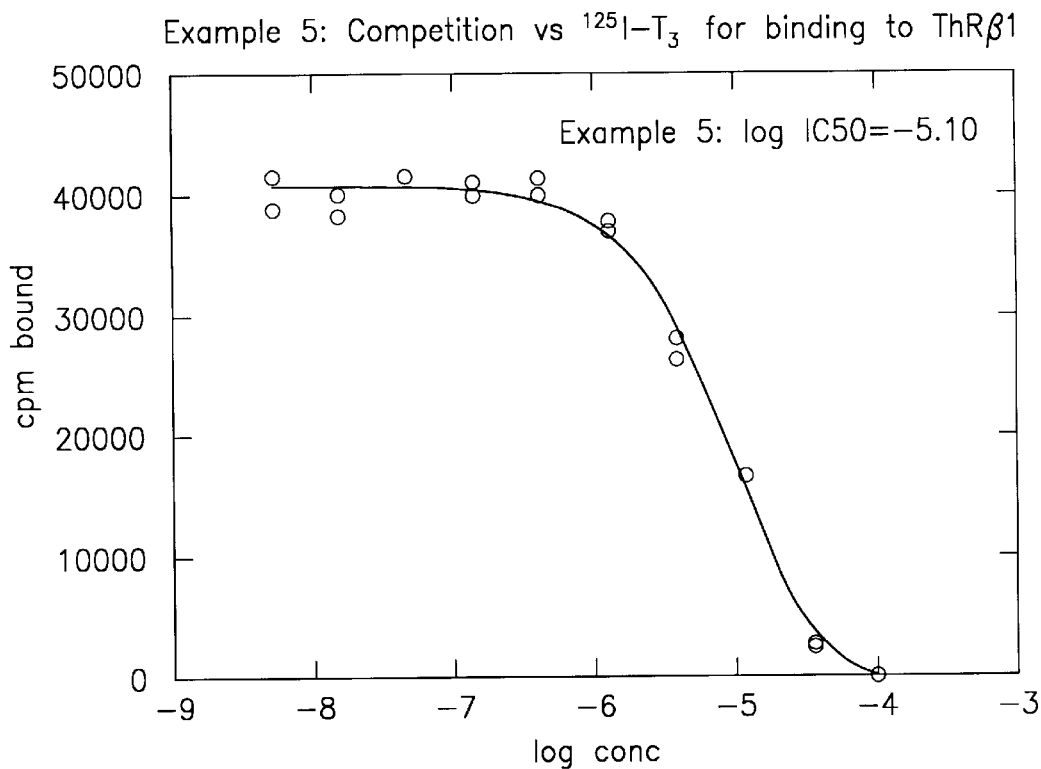
FIG. 37 illustrates competition between 2-n-Butyl-3-(3,5-diiodo-4-carboxymethoxy benzoyl)-5-(4-hydroxybenzamido)benzofuran and $^{125}$I-T$_3$ for binding to ThRβ1.
Figure 38:
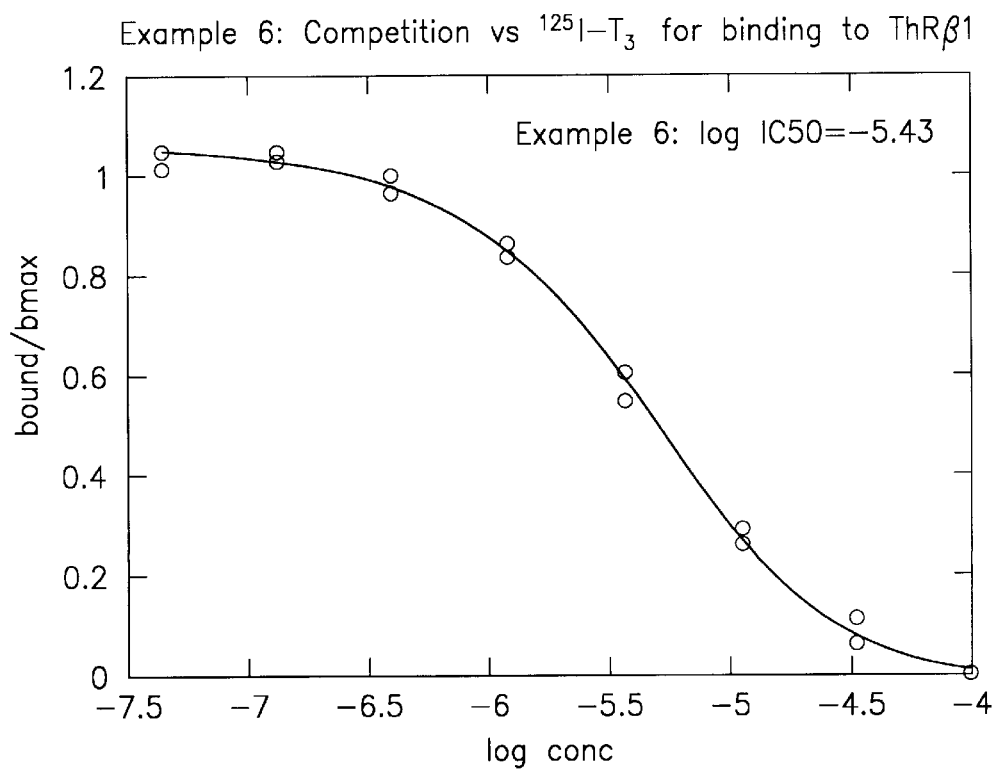
FIG. 38 illustrates the competition between 2-isopropyl-3-(3,5-diiodo-4-carboxymethoxybenzoyl)-5-trifluoromethylsulphonamidobenzofuran and $^{125}$I-T$_3$ for binding to ThRβ1.
Figure 39:
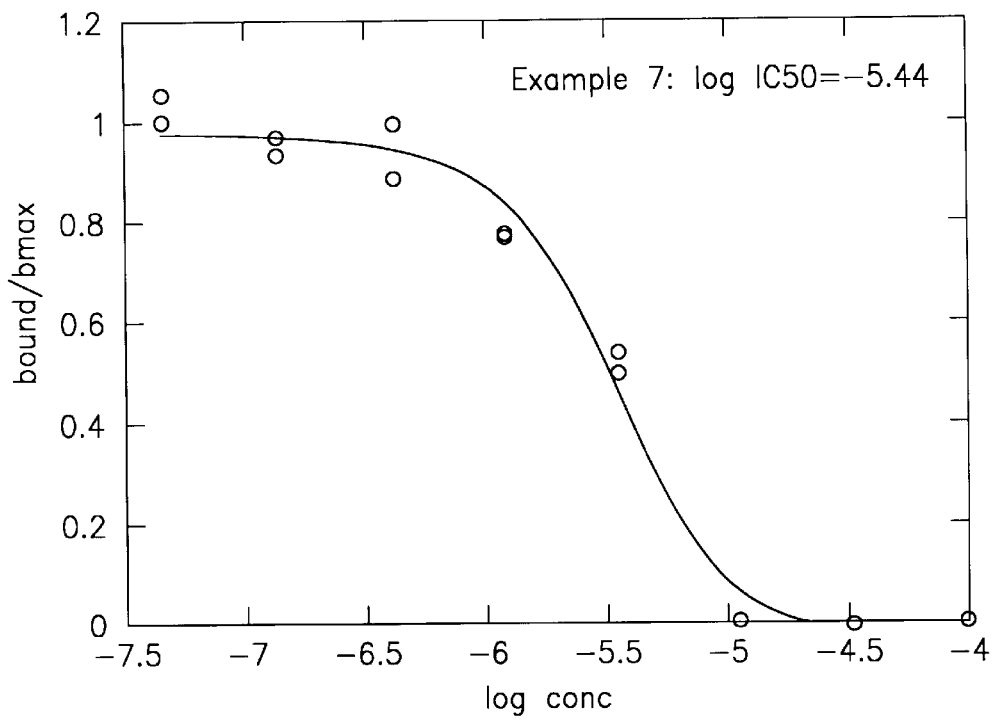
FIG. 39 illustrates the competition between 2-Isopropyl-3-(3,5-diiodo-4-carboxymethoxybenzoyl)-5-(4-methoxybenzamido)benzofuran and $^{125}$I-T$_3$ for binding to ThRβ1.
Figure 40:
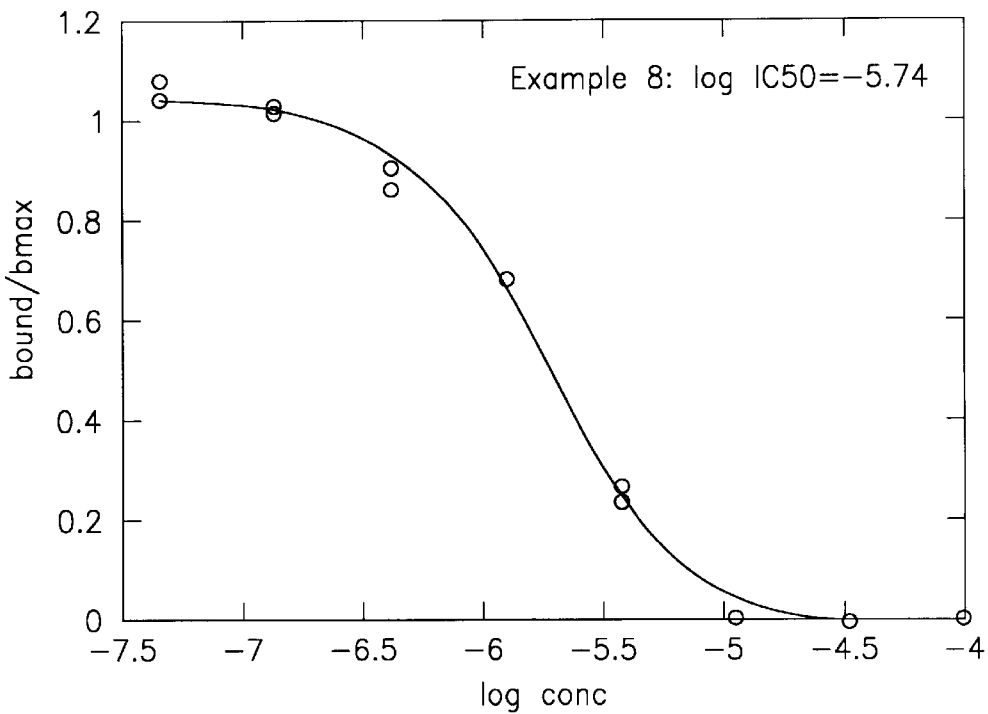
FIG. 40 illustrates competition between 2-Isopropyl-3-(3,5-diiodo-4-carboxymethoxybenzoyl)-5-(4-hydroxybenzamido)benzofuran and $^{125}$I-T$_3$ for binding to ThRβ1.
Figure 41:
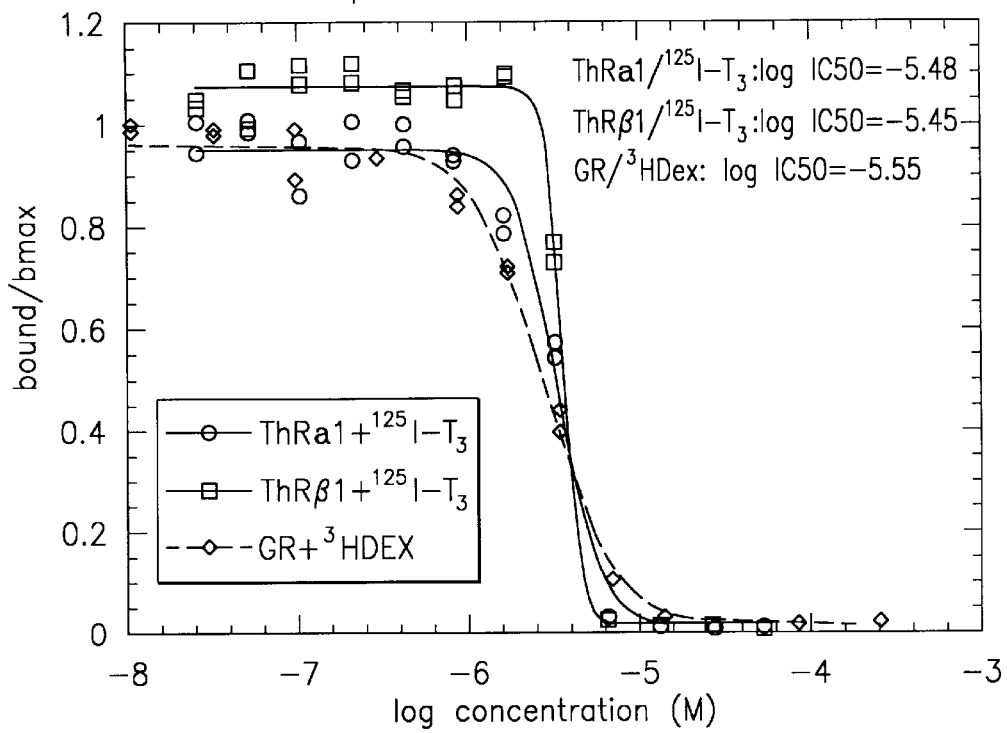
FIG. 41 illustrates competition between 2-n-Butyl-3-(3,5-diiodo-4-carboxymethoxybenzoyl)-5-(4-fluorobenzamido)benzofuran and labelled hormones for binding to nuclear receptors.
Figure 42:
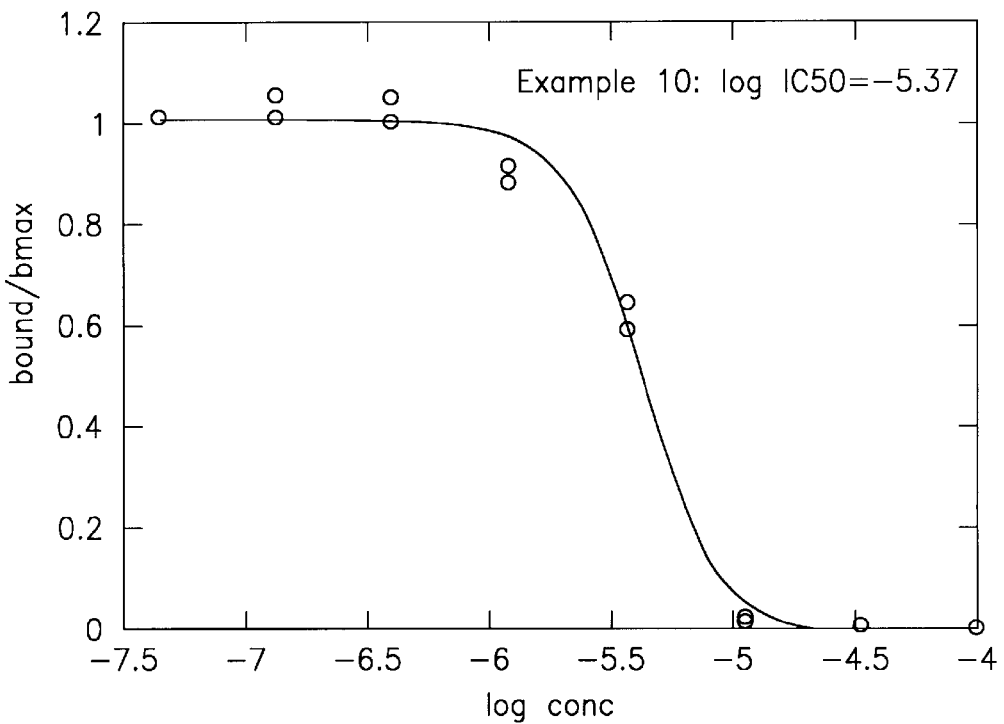
FIG. 42 illustrates competition between 2-Isopropyl-3-(3,5-diiodo-4-carboxymethoxybenzoyl)-5-(4-nitrobenzamido)benzofuran and $^{125}$I-T$_3$ for binding to ThRβ1.
Figure 43:
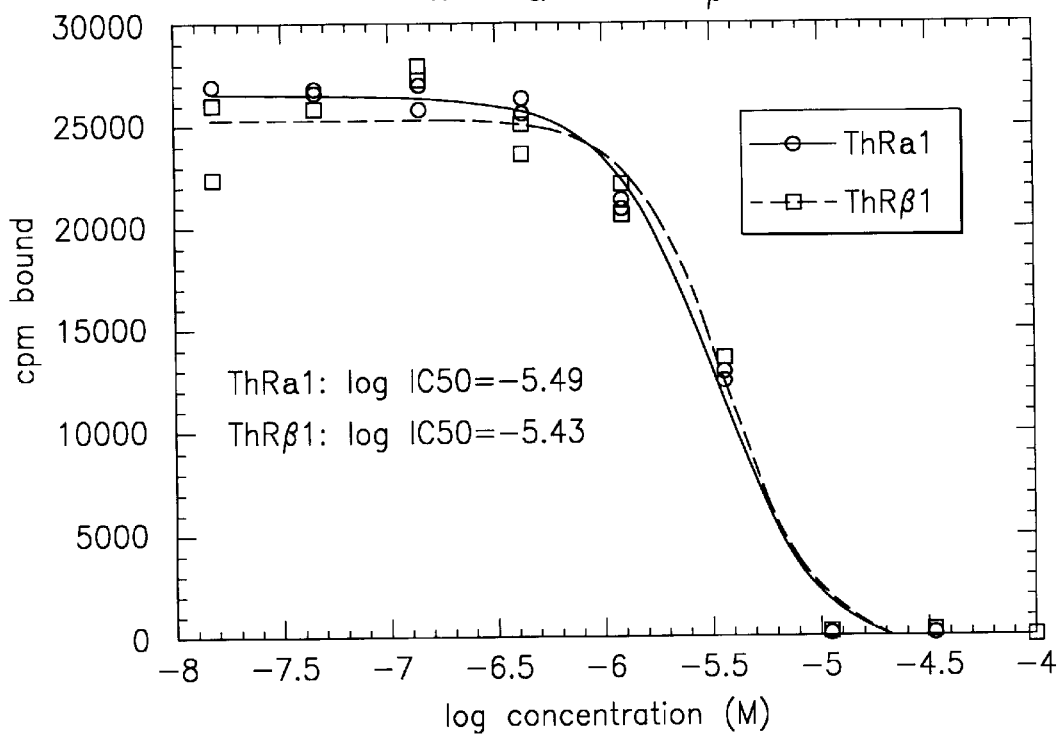
FIG. 43 illustrates competition between 2-n-Butyl-3-(3,5-diiodo-4-carboxymethoxybenzoyl)-5-(4-methoxyphenylureido)benzofuran and $^{125}$I-T$_3$ for binding to ThRβ1.
Figure 44:
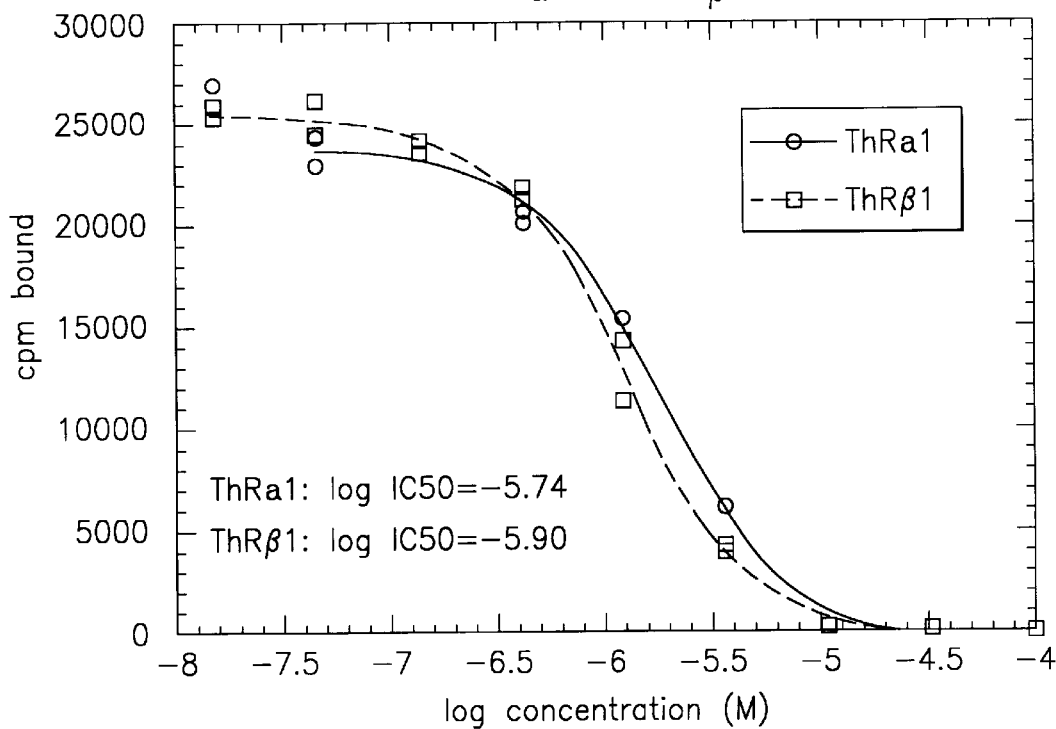
FIG. 44 illustrates competition between 2-n-Butyl-3-(3,5-diiodo-4-carboxymethoxybenzoyl)-5-(4-hydroxyphenylureido)benzofuran and $^{125}$I-T$_3$ for binding to ThRβ1.
Figure 45:
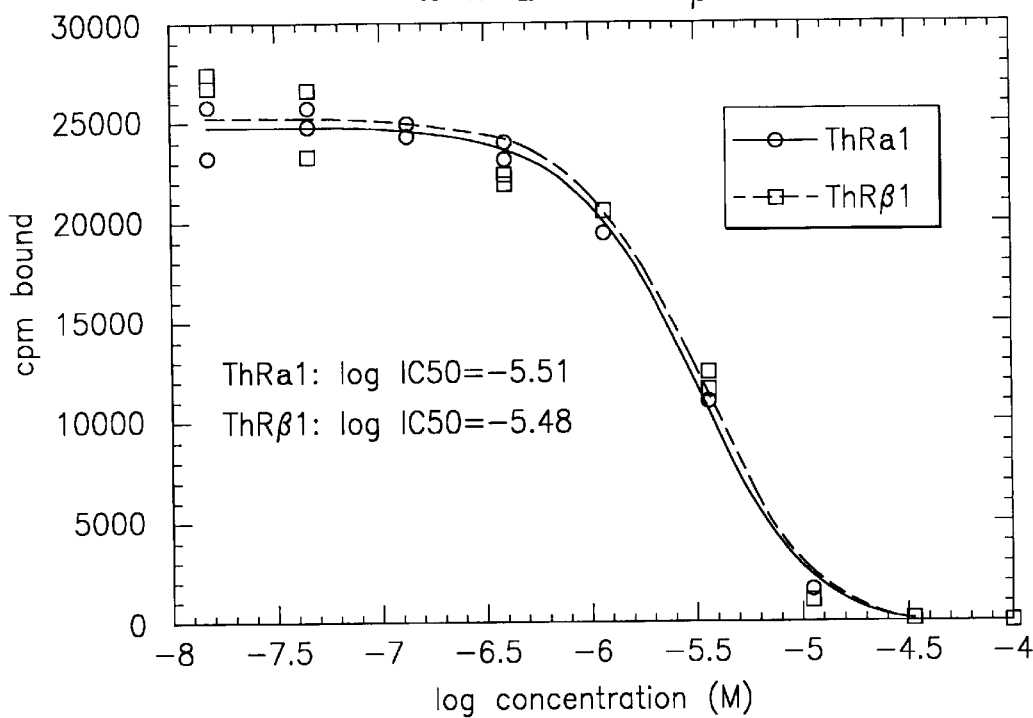
FIG. 45 illustrates competition between 2-n-Butyl-3-(3,5-dibromo-4-carboxymethoxybenzoyl)-5-(4-hydroxybenzamido)benzofuran and $^{125}$I-T$_3$ for binding to ThRβ1.
Figure 46:
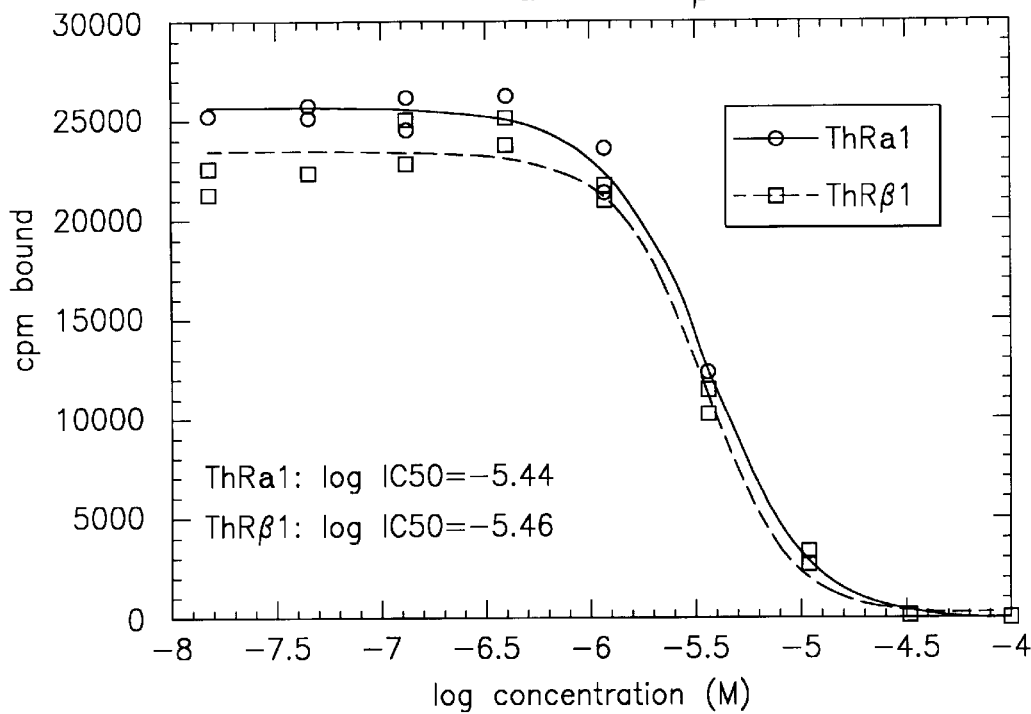
FIG. 46 illustrates competition between 2-Isopropyl-3-(3,5-dibromo-4-carboxymethoxybenzoyl)-5-(4-methoxybenzamido)benzofuran and $^{125}$I-T$_3$ for binding to ThRβ1.
Figure 47:
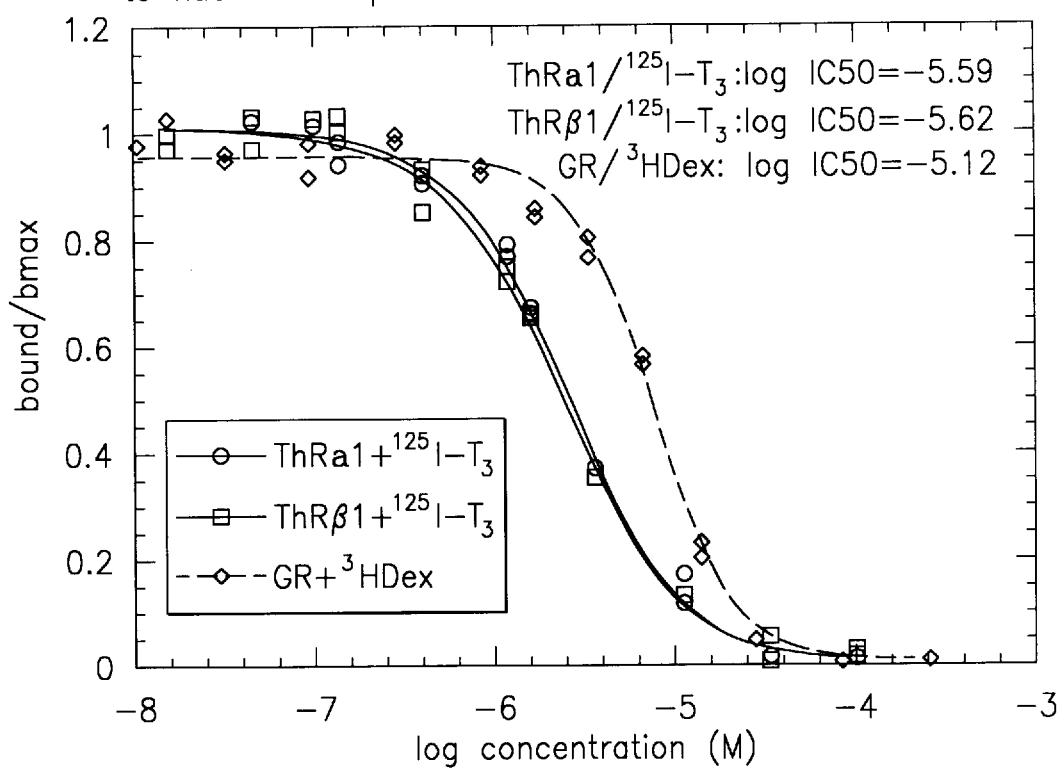
FIG. 47 illustrates competition between 2-Isopropyl-3-(3,5-dibromo-4-carboxymethoxybenzoyl)-5-(4-hydroxybenzamido)benzofuran and labelled hormones for binding to nuclear receptors.

EXAMPLE I 2-n-Butyl-3(3,5-diiodo-4-carboxymethoxybenzoyl)-5-trifluoromethylsulphonamidobenzofuran (a) A solution of 2-hydroxy-5-nitrobenzyl bromide (50 g, 0.216 mol) and triphenylphosphine (56.5 g, 0.216 mol) in chloroform (800 ml) was refluxed for 3 h. After cooling, the resulting solid was filtered off and dried to produce 104 g (yield 98%) of 2-hydroxy-5-nitrobenxyl triphenylphosphine bromide.

(b) The above Wittig salt (49.2 g, 0.1 mol) was mixed with valeryl chloride (15 g, 0.125 mol) and pyridine (16 ml) in chloroform (100 ml). The resulting solution was refluxed for 2 h. The chloroform was removed and replaced by toluene.

Triethylamine (15 ml) was added and the solution was refluxed for 3 h. The precipitated triphenylphosphine oxide was removed by filtration and washed with ethylacetate. The filtrate was concentrated and purified by column chromatography on silica with petroleum ether as eluant. 15 g of pure 2-n-butyl-5 nitrobenzofuran was obtained.

(c) Tin (IV) chloride (13.4 g, 51.3 mmol) was added dropwise to a solution of the above benzofuran (10 g, 45.6 mol) and anisoyl chloride (10 g, 58.6 mmol) in methylene chloride (100 ml). The resulting mixture was stirred at room temperature overnight. 2M hydrochloric acid was added and the organic layer was washed with brine, dried, using $MgSO_4$, and concentrated. The residue was purified by column chromatography on silica with a 9:1 mixture of petroleum ether - ethylacetate as eluant to produce 4 g (yield 59%) of 2-n-butyl-3-(4-methyoxybenzoyl)-5-nitrobenzofuran.

(d) The above methoxy compound (1.5 g, 4.2 mmol) was dissolved in methylene chloride (30 ml), and borontribromide (4.7 ml of a 1M solution in methylene chloride, 4.7 mmol) was added dropwise. The mixture was stirred at room temperature overnight and then quenched with 1M HCl (10 ml). The organic layer was washed with brine, dried using $MgSO_4$, concentrated and purified by column chromatography on silica with a 4:1 mixture of petroleum ether - ethylacetate as eluant to produce 1.0 g (yield 70%) of 2-n-butyl-3-(4-hydroxybenzoyl)-5-nitrobenzofuran.

(e) A solution of iodine (2.1 g, 8.2 mmol) and potassium iodide (1.8 g, 12 mmol) in water (10 ml) was added to a suspension of the above phenol in 25% ammonia (25 mL). The mixture was stirred at room temperature overnight. The reaction mixture was acidified with 6M hydrochloric acid and extracted with ethyl acetate. The organic layer was washed with brine, dried using $MgSO_4$ and concentrated. Recrystallization of the residue from ethylacetate - petroleum ether produced 1.2 g (yield 68%) of 2-n-butyl-3-(3,5-diiodo-4-hydroxybenzoyl)-5-nitrobenzofuran.

(f) The above diiodophenol 1.4 g, 2.3 mmol) was dissolved in dry acetone (20 ml). Potassium carbonate (0.65 g, 4.6 mmol) and ethylbromacetate (0.6 g, 3.5 mmol) were added and the mixture was stirred at room temperature overnight. The reaction mixture was diluted with ethyl acetate and washed with water and brine. The organic layer was dried using $MgSO_4$, and concentrated. Purification by column chromatography on silica with a 9:1 mixture of petroleum ether—ethyl—acetate as eluant produced 1.4 g (yield 90%) of 2-n-butyl-3-(3,5-diiodo-4-ethyl carboxymethoxybenzoyl)-5-nitrobenzofuran.

(g) The above nitrobenzofuran (1.0 g, 1.5 mmol) was dissolved in a mixture of ethyl acetate (10 ml) and ethanol (10 ml). Tin (II) chloride (0.4 g, 1.62 mmol) was added and the resulting mixture was refluxed overnight. After cooling, the mixture was washed with 1M NaOH and brine, dried using $K_2CO_3$ and concentrated.

Purification by column chromatography on silica with a 3:1 mixture of petroleum ether - ethylacetate saturated with ammonia as eluant produced 700 mg (yield 68%) of 5-amino-2-n-butyl-3-(3,5-diiodo-4-ethyl carboxymethoxybenzoyl)-benzofuran.

(h) The above aminobenzofuran (100 mg, 0.15 mmol) was dissolved in methylene chloride (3 ml). Triethylamine (18 mg, 0.18 mmol) and trifluoromethanesulphonyl anhydride (0.51 mg, 0.18 mmol) were added and the resulting mixture was stirred at room temperature for one hour. The reaction mixture was washed with 1M HCl then brine, dried using $MgSO_4$ and concentrated to afford 76 mg (yield 65%) of 2-n-butyl-3-(3 ,5-diiodo-4-ethyl carboxymethoxybenzoyl)-5-trifluoromethylsulphonamidobenzofuran.

(i) The above ester (70 mg, 0.09 mmol) was dissolved in methanol (2 ml), 1M NaOH (0.3 ml) was added and the reaction mixture was stirred at room temperature for 2 h. The mixture was acidified with 2M HCl and diluted with methylene chloride. The organic layer was washed with brine, dried using $MgSO_4$ and concentrated. The residue was purified by preparative TLC on silica plates with a 90:10:1 mixture of methylene chloride—methanol—acetic acid as eluant to produce 50 mg (yield 74%) of pure 2-n-butyl-3-(3,5-diiodo-4-carboxymethoxybenzoyl)-5-trifluoromethylsulphonamidobenzofuran.

EXAMPLE 2

2-n-butyl-3,5-diiodo-4-carboxymethoxybenzoyl)-5-isopropylamidobenzofuran (a) Triethyl amine (18 mg, 0.18 mmol) and isobutyryl chloride (20 mg, 0.18 mmol) were added to a solution of 5-amino-2-n-butyl-3-(3,5-diiodo-4-ethyl carboxymethoxybenzoyl)-benzofuran (prepared as in Example 1(g) (100 mg, 0.15 mmol) in methylene chloride (3 ml). The resulting mixture was stirred at room temperature for 2 h, then washed with brine, dried using $MgSO_4$ and concentrated to produce 60 mg (yield 56%) of 2-n-butyl-3-(3,5-diiodo-4-ethyl carboxymethoxybenzoyl)-5-isopropylamidobenzofuran.

(b) The above ester (60 mg, 0.08 mmol) was hydrolysed and purified by the same method described in Example 1(i) to produce 30 mg (54% of 2-n-butyl-3-(3,5-diiodo-4-ethyl carboxymethoxybenzoyl)-5-trifluoromethylsulphonamidobenzofuran.

EXAMPLE 3

2-n-Butyl-3-(3,5-diiodo-4-carboxymethoxybenzoyl)-5-(4-methoxybenzamido)benzofuran (a) Triethylamine (28 mg, 0.28 mmol) and anisoyl chloride (47 mg, 0.28 mmol) were added to a solution of 5-amino-2-n-butyl-3-(3,5-diiodo-4-ethyl carboxymethoxybenzoyl)-benzofuran (prepared as in Example 1(g) (150 mg, 0.23 mmol) in methylene chloride (5 ml). The resulting mixture was stirred at room temperature overnight, then washed with brine, dried using $MgSO_4$ and concentrated to produce 172 mg (95%) of 2-n-butyl-3-(3,5-diiodo-4-ethyl carboxymethoxybenzoyl)-5-(4-methoxybenzamido) benzofuran.

(b) The above ester (160 mg, 0.20 mmol) was hydrolysed and purified by the method described in Example 1(i) to produce 140 mg (yield 93%) of 2-n-butyl-3-(3,5-diiodo-4-carboxymethoxybenzoyl)-5-(4-methoxybenzamido)benzofuran.

EXAMPLE 4

2-n-Butyl-3-(3,5-diiodo-4-carboxymethoxybenzoyl)-5-(4-hydroxybenzamido)benzofuran (a) 2-n-butyl-3-(3,5-diiodo-4-carboxymethoxybenzoyl)-5-(4-methoxybenzamido)benzofuran (prepared as in Example 3, 150 mg, mmol) was demethylated by the method described in Example 1 (d) to produce 100 mg of 2-n-butyl-3-(3,5-diiodo-4-carboxymethoxybenzoyl-5-(4-hydroxybenzamido)benzofuran.

EXAMPLE 5

2-Isopropyl-3-(3,5-diiodo-4-carboxymethoxybenzyl)-5-trifluoromethylsulphonamidobenzofuran (a) Reaction of 2-hydroxy-5-nitrobenzyl triphenylphosphine bromide (prepared as described in Example 1(a) (40 g, 0.08 mol) and isobutyl chloride (10,6, 0.1. mol) was carried out with the method described in Example 1(b) to produce 19.7 g of 2-isopropyl-5-nitrobenzofuran.

(b) The above benzofuran (5 g, 24.4 mmol) was treated with anisoyl chloride (4.2 g, 24.4 mmol) as described in Example 1(c) to produce 4.2 g (yield 51%) of 2-isopropyl-3-(4-methoxybenzoyl)-5-nitrobenzofuran.

(c) The above nitrobenzofuran (4 g, 11.7 mmol) was reduced by the method described in Example 1(g) to produce 3.5 g (97%) of 5-amino-2-isopropyl-3-(4-methoxybenzoyl)-5-nitrobenzofuran.

(d) A solution of $AlCl_3$ (5.3, 40 mmol) in ether (15 ml) was added slowly to a suspension of $LiAlH_4$ (0.75 g, 20 mmol) in ether (10 ml). The above ketone (3.5 g, 11.0 mmol) dissolved in ether (30 ml) was added dropwise. The resulting mixture was refluxed for one hour then cooled and quenched with water and 1M NaOH, EtOAc was added and the organic layer was decanted and washed with brine, dried using $K_2CO_3$ and concentrated. The residue was purified by column chromatography on silica with a 3:1 mixture of petroleum ether—ethylacetate saturated with ammonia as eluant to produce 3 g of pure 5-amino-2-isopropyl-3-(4-methoxybenzyl)-benzofuran.

(e) The above aminobenzofuran (1.0 g, 3.4 mmol) was treated with trifluoromethanesulphonyl anhydride (1.1. g, 3.8 mmol) as described in Example 1(h). The residue was purified by column chromatography on silica with a 9:1 mixture of petroleum ether—ethylacetate as eluant to produce 1.25 g (yield 94%) of pure 2-isopropyl-3-(4-methoxybenzyl)-5-trifluoromethylsulphonamidobenzofuran.

(f) The above methoxy compound (1.2 g, 3.2. mmol) was treated with borontribromide as described in Example 1(d) to produce 1.0 g, (yield 83%) of 2-isopropyl-3-(-4-hydroxybenzyl)-5-trifluoromethylsulphonamidobenzofuran.

(g) The above phenol (1.0 g, 2.7 mmol) was treated with iodine as described in Example 1(e) to produce 1.1 g (yield 55%) of 2-isopropyl-3-(3,5-diiodo-4-hydroxybenzyl)-5-trifluoromethylsulphonamidobenzofuran.

(h) The above diiodophenol (127 mg, 0.2 mmol) was treated with ethylbromoacetate as described in Example 1(f). Purification by column chromatography on silica with a 4:1 mixture of petroleum ether—ethylacetate 4:1 as eluant produced 100 mg (72%) of 2-isopropyl-3-(3,5-diiode-4-ethyl carboxymethoxybenzyl)-5-trifluoromethylsulphonamidobenzofuran.

(i) The above ester (100 mg, 0.14 mmol) was treated with NaOH as described in Example 1(i) to produce 40 mg (yield 40%) of pure 2-isopropyl-3-(3,5-diiodo-4-carboxymethoxybenzyl)-5-trifluoromethylsulphonamidobenzofuran.

EXAMPLE 6

2-isopropyl-3-(3,5-diiodo-4-carboxymethoxybenzoyl)-5-trifluoromethylsulphonamidobenzofuran (a) Treatment of 2-isopropyl-3-(4-methoxybenzoyl)-5-nitrobenzofuran (prepared as in Example 5(b), 3.0 g, 8.8 mmol) with borontribromide as described in Example 1(d) produced 2.7 g (90%) of 2-isopropyl-3-(4-hydroxybenzoyl)-5-nitrobenzofuran.

(b) The above phenol (3.0 g, 9.2 mmol) was treated with iodine as described in Example 1(e) to produce 3.8 g (yield 72%) of 2-isopropyl-3-(3,5-diiodo-4-hydroxybenzoyl)-5-nitrobenzofuran.

(c) The above diiodophenol (600 mg, 1.0 mmol) was treated with ethylbromoacetate as described in example 1(f) to produce 518 mg (yield 81%) of 2-isopropyl-3-(3,5-diiodo-4-carboxymethoxybenzoyl)-5-nitrobenzofuran.

(d) The above nitrobenzofuran (1.5 g, 2.4 mmol) was reduced by the method described in Example 1(g) to produce 1.0 g (yield 71%) of 5-amino-2-isopropyl-3-(3,5-diiodo-4-ethyl carboxymethoxybenzoyl)-benzofuran.

(e) The above aminobenzofuran (150 mg, 0.26 mmol) was treated with trifluoromethanesulphonyl chloride as described in Example 1(h) to produce 150 mg (yield 75%) of 2-isopropyl-3-(3,5-diiodo-4-ethyl carboxymethoxybenzoyl)-5-trifluoromethylsulphonamidobenzofuran.

(f) The above ester (100 mg, 0.13 mmol) was hydrolysed and purified by the method described in Example 1(i) to produce 40 mg (yield 42%) of pure 2-isopropyl-3-(3,5-diiodo-4-carboxymethoxybenzoyl)-5-trifluoromethylsulphonamidobenzofuran.

EXAMPLE 7

2-Isopropyl-3-(3,5-diiodo-4-carboxymethoxybenzoyl)-5-(4-methoxybenzamido)benzofuran (a) 5-amino-2-isopropyl-3-(3,5-diiodo-4-ethyl carboxymethoxybenzoyl)-benzofuran (prepared as in Example 6(d), 150 mg, 0.25 mmol) was treated with anisoyl chloride as described in Example 3(a) to produce 160 mg (yield 83%) of 2-isopropyl-3-(3,5-diiodo-4-ethyl carboxymethoxybenzoyl)-5-(4-methoxybenzamido)benzofuran.

(b) The above ester (100 mg, 0.13 mmol) was hydrolysed and purified by the method described in Example 1(i) to produce 60 mg (yield 62%) of pure 2-isopropyl-3-(3,5-diiodo-4-carboxymethoxybenzoyl)-5-(4-methoxybenzamido)benzofuran.

EXAMPLE 8

2-Isopropyl-3-(3,5-diiodo-4-carboxymethoxybenzoyl)-5-(4-hydroxybenzamido)benzofuran (a) 2-isopropyl-3-(3,5-diiodo-4-carboxymethoxybenzoyl)-5-(4-hydroxybenzamido)benzofuran (prepared as in Example 7(b), 40 mg, 0.05 mmol) was treated with borontribromide as described in Example 1(d) to afford 20 mg (55%) of 2-isopropyl-3-(3,5-diiodo-4-carboxymethoxybenzoyl)-5-(4-hydroxybenzamido)benzofuran.

EXAMPLE 9

2-n-Butyl-3-(3,5-diiodo-4-carboxymethoxybenzoyl)-5-(4-fluorobenzamido)benzofuran (a) 5-amino-2-n-butyl-3-(3,5-diiodo-4-carboxymethoxybenzoyl)benzofuran (prepared as in Example 1(g), 70 mg, 0.11 mmol) was treated with 4-fluorobenzoyl chloride by the same method as described in Example 3(a) to produce 60 mg (yield 74%) of 2-n-butyl-3-(3,5-diiodo-4-ethyl carboxymethoxybenzoyl)-5-(4-fluorobenzamido)benzofuran.

(b) The above ester (60 mg, 0.08 mmol) was hydrolysed and purified by the method described in Example 1(i) to produce 30 mg (yield 52%) of pure 2-n-butyl-3-(3,5-diiodo-4-carboxymethoxybenzoyl)-5-(4-fluorobenzamido)benzofuran.

EXAMPLE 10

2-Isopropyl-3-(3,5-diiodo-4-carboxymethoxybenzoyl)-5-(4-nitrobenzamido)benzofuran (a) 5-amino-2-isobutyl-3-(3,5-diiodo-4-carboxymethoxybenzoyl)benzofuran (prepared as in Example 6(d), 1.5 g, 2.4 mmol) was treated with 4-nitrobenzoyl chloride by the same method described in Example 3(a) to produce 60 mg (yield 74%) of 2-isopropyl-3-(3,5-diiodo-4-carboxymethoxybenzoyl)-5-(4-nitrobenzamido)benzofuran.

(b) The above ester (100 mg, 0.13 mmol) was hydrolysed and purified by the method described in Example 1(i) to produce 50 mg (yield 51%) of pure 2-isopropyl-3-(3,5-diiodo-4-carboxymethoxybenzoyl)-5-(4-nitrobenzamido)benzofuran.

EXAMPLE 11

2-n-Butyl-3-(3,5-diiodo-4-carboxymethoxybenzoyl)-5-(4-methoxyphenylureido)benzofuran (a) A solution of 5-amino-2-n-butyl-3-(3,5-diiodo-4-ethylcarboxymethoxybenzoyl)-benzofuran (prepared as in Example 1(g), 320 mg, 0.5 mmol) and p-methoxyphenylisocyanate (75 mg, 0.5 mmol) in THF (10 mL) was stirred at room temperature for 3 h. The mixture was concentrated, ethyacetate was added and the organic layer was washed with water, 1M HCl, then NaHCO₃(sat) then brine, dried using MgSO₂ and then concentrated. Purification by column chromathography on silica with a 95:5 mixture of methylenechloride—methanol as eluant produced 300 mg (75%) of 2-n-butyl-3-(3,5-diiodo-4-ethyl carboxymethoxybenzoyl)-5-(4-methoxyphenylureido)benzofuran.

(b) The above ester (300 mg, 0.36 mmol) was hydrolysed and purified by the method described in 1(i) to produce 240 mg (87%) of 2-n-butyl-3-(3,5-diiodo-4-carboxymethoxybenzoly)-5-(4-methoxyphenylureido) benzofuran.

EXAMPLE 12

2-n-Butyl-3-(3,5-diiodo-4-carboxymethoxybenzoyl)-5-(4-hydroxyphenylureido)benzofuran (a) 2-n-Butyl-3-(3,5-diiodo-4-carboxymethoxybenzoyl)-5-(4-methoxyphenylureido)benzofuran (prepared as in Example 11, 150 mg, 0.2 mmol) was demethylated by the method described in Example 1(d) and purified by preparative TLC on silica plates with a 90:10:1 mixture of methylenechloride—methanol—acetic acid as eluant to produce 100 mg (67%) of 2-n-butyl-3-(3,5-diiodo-4-carboxymethoxybenzoyl)-5-(4-hydroxyphenylureido)benzofuran.

EXAMPLE 13

2-n-Butyl-3-(3,5-dibromo-4-carboxymethoxybenzoyl)-5-(4-hydroxybenzamido)benzofuran (a) 2-n-butyl-3-(4-hydroxybenzoyl)-5-nitrobenzofuran (prepared as in Example 1(d), (1.0 g, 3.2 mmol) was treated with bromine as described in Example 14(a) below to produce 1.2 g (81%) of 2-n-butyl-3-(3,5-dibromo-4-hydroxybenzoyl)5-nitrobenzofuran.

(b) The above dibromophenol (1.3 g, 2.7 mmol) was treated with ethylbromoacetate as described in Example 1(f) to produce 1.4 g (92%) of 2-n-butyl-3-(3,5-dibromo-4-ethyl carboxymethoxybenzoyl)-5-nitrobenzofuran.

(c) The above nitrobenzofuran (350 mg, 0.6 mmol) was reduced by the method described in Example 1(g) to produce 300 mg (90%) of 5-amino-2-n-propyl-3-(3,5-dibromo-4-ethyl carboxymethoxybenzoyl)benzofuran.

(d) The above aminobenzofuran (300 mg, 0.54 mmol) was treated with anisoyl chloride as described in Example 3(a) to produce 320 mg (86%) of 2-n-butyl-3-(3,5-dibromo-4-ethyl carboxymethoxybenzoyl)-5-(4-methoxybenzamido)benzofuran.

(e) The above ester (300 mg, 0.36 mmol) was hydrolysed and purified by the method described in 1(i) to produce 240 mg (85%) of 2-n-butyl-3-(3,5-dibromo-4-carboxymethoxybenzoyl)-5-(4-methoxybenzamido) benzofuran.

(f) The above methoxycompound (80 mg, 0.1 mmol) was demethylated by the method described in Example 1(d) and purified by preparative TLC on silica plates with a 90:10:1 mixture of methylenechloride—methanol—acetic acid as eluant to produce 40 mg (51%) of 2-n-butyl-3-(3,5-dibromo-4-carboxymethoxybenzoyl)-5-(4-methoxybenzamido)benzofuran.

EXAMPLE 14

2-Isopropyl-3-(3,5-dibromo-4-carboxymethoxybenzoyl)-5-(4-methoxybenzamido)benzofuran (a) 2-isopropyl-3-(4-hydroxybenzoyl)-5-nitrobenzofuran (prepared as in Example 6(a), 3.25 g, 10 mmol) was dissolved in acetonitrile (50 mL). Bromine (3.4 g, 21 mmol) was added dropwise and the mixture was stirred at room temperature for 2 h. The mixture was concentrated, ethylacetate was added and the organic layer was washed with water, dried using MgSO₄ and concentrated. Purification by column chromatography on silica with a 1:4 mixture of ethylacetate-petroleum ether as eluant produced 4.7 g (97%) of 2-isopropyl-3-(3,5-dibromo-4-hydroxybenzoyl)5-nitrobenzofuran.

(b) The above dibromophenol (4.7 g, 9.7 mmol) was treated with ethylbromoacetate as described in Example 1(f) to produce 5.1 g (90%) of 2-isopropyl-3-(3,5-dibromo-4-ethyl carboxymethoxybenzoyl)-5-nitrobenzofuran.

(c) The above nitrobenzofuran (5.1 g, 8.8 mmol) was reduced by the method described in Example 1(g) to produce 4.2 g (87%) of 5-amino-2-isopropyl-3-(3,5-dibromo-4-ethyl carboxymethoxybenzoyl)-benzofuran.

(d) The above aminobenzofuran (570 mg, 1.0 mmol) was treated with anisoyl chloride as described in Example 3(a) to produce 640 mg (95%) of 2-isopropyl-3-(3,5-dibromo-4-ethyl carboxymethoxybenzoyl)-5-(4-methoxybenzamido)benzofuran.

(e) The above ester (200 mg, 0.3 mmol) was hydrolysed and purified by the method described in Example 1(i) to produce 160 mg (83%) of 2-isopropyl-3-(3,5-dibomo-4-carboxymethoxybenzoyl)-5-(4-methoxybenzamido)benzofuran.

EXAMPLE 15

2-Isopropyl-3-(3,5-dibromo-4-carboxymethoxybenzoyl)-5-(4-hydroxybenzamido)benzofuran (a) 2-isopropyl-3-(3,5-dibromo-4-ethyl carboxymethoxybenzoyl)-5-(4-methoxybenzamido) benzofuran (prepared as in Example 13(d), 400 mg, 0.59 mmol) was treated with borontribomide as described in Example 1(d) and purified by preparative TLC on silica plates with a 90:10:1 mixture of methylenechloride—methanol—acetic acid as eluant to produce 200 mg (51%) of 2-isopropyl-3-(3,5-dibromo-4-carboxymethoxybenzoyl)-5-(4-hydroxybenzamido)benzofuran.

RESULTS

BIOLOGICAL ACTIVITY

The biological activity of compounds in accordance with the invention was tested in thyroid hormone responsive reporter cell lines.

The thyroid hormone reporter cell lines (TRAF α and TRAF β) are genetically engineered, mammalian cell lines expressing thyroid hormone receptor (ThR) α and β, respectively. These thyroid hormone responding cell lines contain stable integrated artificial transcription units comprised of a thyroid hormone response element (TRE) and core promoter sequences fused to a downstream reporter gene encoding a secreted form of alkaline phosphatase (ALP).

In the absence of thyroid hormone the cells express only very low levels of the ALP reporter protein. However, following exposure of the TRAF α or β cells to thyroid hormones like e.g. T3 the ThR is activated resulting in transcriptional activation of the ALP reporter gene, mediated through the TRE. The expression of the ALP reporter protein in the TRAFα and TRAFα reporter cell lines, respectively, is induced by its natural agonist T3 in a concentration dependent manner. The expression of the ALP reporter protein in the TRAFα and TRAFβ reporter cell lines, respectively, is induced by its natural agonist T3 in a concentration dependent manner. The level of thyroid hormone dependent ALP protein expressed can be determined indirectly by an enzymatic chemiluminescence assay as previously described (*Advances in Steroid Analysis* '93, editor: Görög S., Proceedings of the 5th Symposium on the analysis of Steroids, Published by Akadémiai Kiado, Budapest, Hungary, p. 57–67). Briefly, an aliquot of the conditioned cell culture medium is mixed with AMPPD (disodium 3–4-methoxyspiro(1,2-dioxetane-3,2'-tricyclo(3, 3.1)decan)-4-yl) phenyl phosphate containing assay buffer and incubated at 37° C. for 20 minutes. AMPPD was purchased from Boule Diagnostic, Sweden. The ALP in the medium sample dephosphorylates AMPPD generating an unstable intermediate which decomposes and emits light which is measured in a microplate format luminometer (Luminoskan, Labsystems, Finland). The rate of light emission is directly proportional to the level of ALP present in the sample.

Since the TRAF α and β cells, respectively, show a stringent dependence on the presence of a thyroid hormone agonist for expression of the ALP reporter protein, the cells have to be stimulated by a low concentration of reference agonist (3,5,3'-triodothyronine (T3), Sigma) in order to analyse compounds for their antagonistic activity.

Using the above described reporter cell lines, the synthesized thyroid hormone derivatives were tested (±T3 (reference agonist)) for their capacity to influence, via interaction with the human thyroid hormone receptors α and β, respectively, the transcriptional activity of the ALP reporter gene i.e. their agonistic/antagonistic activity.

EXPERIMENTAL DESIGN

Day 1

The TRAF α and β cells, respectively, were seeded at a density of $2-2.5\times10^4$ cells/well in 96-well microtiterplates (suitable for growth of mammalian cells). The cells were seeded in Coon's medium (without phenolred) (SVA, Uppsala, Sweden)+10% FCS (Gibco-BRL) (hormone stripped) and cultivated overnight at 37° C. and 5% $CO_2$ in a humidified incubator.

Day 2

Change of medium to Coon's medium (without phenol red)+5% serum substitute (Dr. Alan Preston, Med. Vet Supplies Limited, Botolth Clayton, Buckingham, MK18 2LR, U.K.)±T3 and test compounds (see below). The cells were then cultivated at 37° C. and 5% $CO_2$ in a humidified incubator for an additional 48 hours.

Day 4

48 hours post addition of the hormonal/test compounds, cell number and cell morphology were examined under the light-microscope. A 10 μl aliquot of conditioned medium from each well was then transferred to white microtiterplates and assayed for the level of ALP reporter protein expressed (as described in *Advances in Steroid Analysis* '93 above). In addition, the cell toxic effect of compounds was determined by the colorimetric MTS/PMS assay according to the suppliers recommendation (Promega Corp. through Scandinavian Diagnostic Services, Sweden)

Hormone/test compounds added to the TRAF α and β reporter cells, respectively, per well in 96-well microtiter plates Test on cells for response to increasing concentration of T3 [reference agonist (ref. ag.)] (3 wells/concentration):

concentration range: from $10^{-11}$ to $10^{-6}$M T3 as indicated on the x-axis, vehicle only (no T3 added) appears as $10^{-12}$M on the x-axis.

Test on cells for response to increasing concentration of test compound±1 nM T3 (ref. ag.) (3 wells/concentration):

test for agonist activity (in the absence of T3 addition):
concentration range (example 1–3, 5): from $10^{-9}$ to $10^{-5}$M test compound as indicated on the x-axis, vehicle only (no test compound added) appears as $10^{-10}$M on the x-axis;
concentration range (example 4): from $10^{-8}$ to $4\times10^{-5}$M test compound as indicated on the x-axis, vehicle only (no test compound added) appears as $10^{-9}$M on the x-axis;
concentration range (example 6): from $10^{-7}$ to $4\times10^{-5}$M test compound as indicated on the x-axis, vehicle only (no test compound added) appears as $10^{-8}$M on the x-axis;
concentration range (example 7–10): from $5\times10^{-9}$ to $2\times10^{-5}$M test compound as indicated on the x-axis, vehicle only (no test compound added) appears as $10^{-9}$M on the x-axis;
concentration range (example 11–14): from $10^{-7}$ to $3.2\times10^{-5}$M test compound as indicated on the x-axis, vehicle only (no test compound added) appears as $10^{-8}$M on the x-axis;
concentration range (example 15): from $10^{-7}$ to $6.4\times10^{-5}$M test compound as indicated on the x-axis, vehicle only (no test compound added) appears as $10^{-8}$M on the x-axis;
test for antagonist activity (in the presence of 1 nM T3):
concentration range (example 1–3, 5): from $10^{-9}$ to $10^{-5}$M test compound as indicated on the x-axis in the presence of 1 nM T3, vehicle and 1 nM T3 only (no test compound added) appears as $10^{-10}$M on the x-axis;
concentration range (example 4): from $10^{-8}$ to $4\times10^{-5}$M test compound as indicated on the x-axis in the presence of 1 nM T3, vehicle and 1 nM T3 only (no test compound added) appears as $10^{-9}$M on the x-axis;
concentration range (example 6): from $10^{-7}$ to $4\times10^{-5}$M test compound as indicated on the x-axis in the presence of 1 nM T3, vehicle and 1 nM T3 only (no test compound added) appears as $10^{-8}$M on the x-axis;
concentration range (example 7–10): from $5\times10^{-9}$ to $2\times10^{-5}$M test compound as indicated on the x-axis in the presence of 1 nM T3, vehicle and 1 nM T3 only (no test compound added) appears as $10^{-9}$M on the x-axis;
concentration range (example 11–14): from $10^{-7}$ to $3.2\times10^{-5}$M test compound as indicated on the x-axis in the presence of 1 nM T3, vehicle and 1 nM T3 only (no test compound added) appears as $10^{-8}$M on the x-axis; and
concentration range (example 15): from $10^{-7}$ to $6.4\times10^{-5}$M test compound as indicated on the x-axis in the presence of 1 nM T3, vehicle and 1 nM T3 only (no test compound added) appears as $10^{-8}$ M on the x-axis.

Affinity tests

A series of dilutions of each compound produced (Examples 1–15) were allowed to compete with a fixed concentration (0.2 nM) of $^{125}$I-T$_3$ for binding to the human thyroid hormone receptor β1 (ThRβ1). In some examples, binding to the human thyroid hormone receptor α1 (ThRα1) was included.

After reaching equilibrium a separation step on Sephadex-G25 columns was introduced whereby the receptors were separated from compounds of low molecular weight (i.e the radioactive labeled hormones). The eluated receptor bound radioactivity was measured in a gamma-counter or with regular liquid scintillation counting.

An IC$_{50}$-value (The concentration of compound required to inhibit 50% of the binding of radioactive labeled hormone) was calculated from the curves. The resulting IC$_{50}$-values expressed as logarithmic units are shown in table 1.

TABLE 1

|  | vs T3 for TRα1 log IC50 | vs T3 for ThRβ1 log IC50 |
| --- | --- | --- |
| Example 1 |  | −5.65 |
| Example 2 |  | −5.18 |
| Example 3 |  | −5.82 |
| Example 4 | −5.60 | −5.69 |
| Example 5 |  | −5.1 |
| Example 6 |  | 5.43 |
| Example 7 |  | −5.44 |
| Example 8 |  | −5.74 |
| Example 9 | −5.48 | −5.45 |
| Example 10 |  | −5.37 |
| Example 11 | −5.49 | −5.43 |
| Example 12 | −5.74 | −5.9 |
| Example 13 | −5.59 | −5.62 |
| Example 14 | −5.44 | −5.46 |
| Example 15 | −5.51 | −5.48 |

Conclusions:

The range of affinities for the ThRβ1 is between $10^{-5.10}$M. to $10^{-5.90}$M.

The differences in affinities for the investigated compounds binding to ThRα1 or to ThRβ1 are relatively small.

The above results show that most compounds showed at least weak antagonism to T3 at a high dose.

Three compounds (example 1,2 and 5) showed no antagonism to T3 in the ThRα reporter cell line but rather a concentration dependent augmention of the agonism of T3. Only example 5 displayed a similar activity in the ThRβ reporter cell line. One compound (example 11) showed partial agonist/antagonist activity in both ThRα and β reporter cell lines. Two compounds (example 14 and 15) had a partial agonist/antagonist activity in the ThRα reporter cell line but no or only weak antagonist activity in the ThRβ reporter cell line.

I claim:

1. Compounds according to the formula:

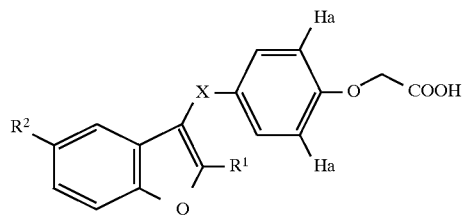

in which:
Ha=I or Br;
X=CH$_2$ or C=O;
R$^1$=C$_{1-4}$ alkyl;
R$^2$=−NHSO$_2$R$^3$; —NHCOR$^3$; or —NHCONHR$^3$;
where R$^3$=−CF$_3$, C$_{1-4}$ alkyl, or 4-R$^4$C$_6$H$_4$—;
where R$^4$=C$_{1-4}$ alkoxy-; hydroxy-; fluoro-; or nitro-; or a pharmaceutically acceptable salt thereof.

2. A compound according to claim 1 selected from 2-n-butyl-3-(3,5-diiodo-4-carboxymethoxybenzoyl)-5-trifluoromethylsulphonamidobenzofuran; 2-n-butyl-3,5-diiodo-4-carboxymethoxybenzoyl)-5-isopropylamidobenzofuran; 2-n-butyl-3-(3,5-diiodo-4-carboxymethoxybenzoyl)-5-(4-methoxybenzamido) benzofuran; 2-n-Butyl-3-(3,5-diiodo-4-carboxymethoxybenzoyl)-5-(4-hydroxybenzamido)

benzofuran; 2-Isopropyl-3-(3,5-diiodo-4-carboxymethoxybenzyl)-5-trifluoromethylsulphonamidobenzofuran; 2-isopropyl-3-(3,5-diiodo-4-carboxymethoxybenzoyl)-5-trifluoromethylsulphonamidobenzofuran; 2-Isopropyl-3-(3,5-diiodo-4-carboxymethoxybenzoyl)-5-(4-methoxybenzamido)benzofuran; 2-Isopropyl-3-(3,5-diiodo-4-carboxymethoxybenzoyl)-5-(4-hydroxybenzamido)benzofuran; 2-n-Butyl-3-(3,5-diiodo-4-carboxymethoxybenzoyl)-5-(4-fluorobenzamido)benzofuran; 2-Isopropyl-3-(3,5-diiodo-4-carboxymethoxybenzoyl)-5-(4-nitrobenzamido)benzofuran; 2-n-Butyl-3-(3,5-diiodo-4-carboxymethoxybenzoyl)-5-(4-methoxyphenylureido)benzofuran; 2-n-Butyl-3-(3,5-diiodo-4-carboxymethoxybenzoyl)-5-(4-hydroxyphenylureido)benzofuran; 2-n-Butyl-3-(3,5-dibromo-4-carboxymethoxybenzoyl)-5-(4-hydroxybenzamido)benzofuran; 2-Isopropyl-3-(3,5-dibromo-4-carboxymethoxybenzoyl)-5-(4-methoxybenzamido)benzofuran; and 2-Isopropyl-3-(3,5-dibromo-4-carboxymethoxybenzoyl)-5-(4-hydroxybenzamido)benzofuran.

3. A pharmaceutical composition comprising an effective amount of a compound according to any one of claims 1 to 2, or a pharmaceutically effective salt thereof, together with a suitable carrier.

4. A method of treatment of a patient with a T-3-regulated gene disorder or disease, comprising administering an effective amount of a compound, according to any one of claims 1 to 3 or a pharmaceutically acceptable salt thereof, or a pharmaceutical according to claim 3, to the patient.

5. A method of treatment according to claim 4 in which the disorder or disease is selected from the group consisting of heart arrhythmia, heart failure, and hyperthyroidism.

6. Compounds according to the formula:

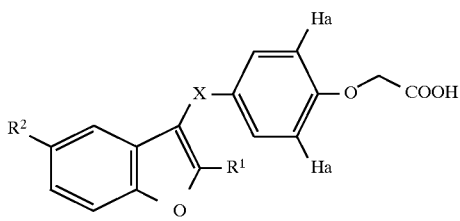

in which:
Ha=I or Br;
X=CH$_2$ or C=O;
R=C$_{1-4}$ alkyl;
R$^2$=—NHSO$_2$R$^3$; —NHCOR$^3$; or —NHCONHR$^3$;
where R$^3$=—CF$_3$, C$_{1-4}$ alkyl, or 4-R$^4$C$_6$H$_4$—;
where R$^4$=C$_{1-4}$ alkoxy-; hydroxy-; fluoro-; or nitro-; or a pharmaceutically acceptable salt thereof;
and wherein said compounds are selected from the group consisting of 2-n-butyl-3-(3,4-diiodo-4-carboxymethoxybenzoyl)-5-(4-methoxybenzamido)benzofuran and 2-n-butyl-3-(3,4-diiodo-4-carboxymethoxybenzoyl)-5-(4-hydroxybenzamido)benzofuran.

7. A pharmaceutical composition comprising an effective amount of a compound according to claim 6 or a pharmaceutically effective salt thereof, together with a suitable carrier.

8. A method of treatment of a patient with a T-3-regulated gene disorder or disease, comprising administering to the patient an effective amount of a compound according to claim 6 or a pharmaceutical composition according to claim 7.

9. The method of claim 8, wherein the disorder or disease is selected from the group consisting of heart arrhythmia, heart failure, and hyperthyroidism.

* * * * *